(12) United States Patent
Bacon et al.

(10) Patent No.: US 8,314,155 B2
(45) Date of Patent: Nov. 20, 2012

(54) BICYCLIC AROMATIC SULFINYL DERIVATIVES

(75) Inventors: Edward R. Bacon, Audubon, PA (US); Sankar Chatterjee, Wynnewood, PA (US); Mohamed Iqbal, Malvern, PA (US); Brigitte Lesur, Saint Germaine en Laye (FR); Philippe Louvet, Vert-le-petit (FR)

(73) Assignees: Cephalon, Inc, Frazer, PA (US); Cephalon France, Maisons-Alfort Cedex (FR)

( * ) Notice: Subject to any disclaimer, the term of this patent is extended or adjusted under 35 U.S.C. 154(b) by 1151 days.

(21) Appl. No.: 12/214,567

(22) Filed: Jun. 20, 2008

(65) Prior Publication Data
US 2009/0042907 A1 Feb. 12, 2009

Related U.S. Application Data

(62) Division of application No. 11/104,237, filed on Apr. 12, 2005, now Pat. No. 7,423,176.

(60) Provisional application No. 60/568,965, filed on May 7, 2004.

(30) Foreign Application Priority Data

Apr. 13, 2004 (EP) .................................. 04290985

(51) Int. Cl.
C07C 323/52 (2006.01)
C07C 323/60 (2006.01)
C07C 317/44 (2006.01)
C07D 295/18 (2006.01)
C07D 311/74 (2006.01)
C07D 405/12 (2006.01)
C07D 335/06 (2006.01)
C07D 207/16 (2006.01)
C07D 211/46 (2006.01)

(52) U.S. Cl. ........................................ 514/708; 514/709
(58) Field of Classification Search .................. None
See application file for complete search history.

(56) References Cited

U.S. PATENT DOCUMENTS

| | | | |
|---|---|---|---|
| 3,821,277 A | 6/1974 | Koenig et al. |
| 4,177,290 A | 12/1979 | Lafon |
| 4,617,309 A | 10/1986 | Bottcher et al. |
| 4,728,647 A | 3/1988 | Benavides et al. |
| 4,744,812 A | 5/1988 | Parg et al. |
| 4,769,461 A | 9/1988 | Musser et al. |
| 4,788,199 A | 11/1988 | Benavides et al. |
| 4,788,204 A | 11/1988 | Benavides et al. |
| 4,952,235 A | 8/1990 | Andre et al. |
| 5,149,703 A | 9/1992 | Lau et al. |
| 5,180,745 A | 1/1993 | Lafon |
| 5,401,776 A | 3/1995 | Laurent |
| 5,561,227 A | 10/1996 | Thiruvengadan et al. |
| 5,563,169 A | 10/1996 | Yoshida et al. |
| 5,612,379 A | 3/1997 | Laurent |
| 5,719,168 A | 2/1998 | Laurent |
| 5,744,339 A | 4/1998 | Chatterjee |
| 6,251,917 B1 | 6/2001 | Lubish et al. |
| 6,346,548 B1 | 2/2002 | Miller et al. |
| 6,455,588 B1 | 9/2002 | Scammell et al. |
| 6,472,414 B1 | 10/2002 | Biller et al. |
| 6,488,164 B2 | 12/2002 | Miller et al. |
| 6,492,396 B2 | 12/2002 | Bacon et al. |
| 6,498,196 B1 | 12/2002 | Roberts et al. |
| 6,670,358 B2 | 12/2003 | Bacon et al. |
| 6,919,367 B2 | 7/2005 | Bacon et al. |
| 6,924,314 B2 | 8/2005 | Sharma et al. |
| 7,119,214 B2 | 10/2006 | Lesur et al. |
| 2002/0045629 A1 | 4/2002 | Bacon et al. |
| 2002/0143052 A1 | 10/2002 | Lan-Hargest et al. |
| 2003/0191112 A1 | 10/2003 | Dorwald |

FOREIGN PATENT DOCUMENTS

| | | |
|---|---|---|
| CA | 2011834 | 3/1990 |
| DE | 28 12 542 | 10/1979 |
| EP | 0 001 989 | 10/1978 |
| EP | 1 411 052 | 7/2002 |
| GB | 1 368 227 | 9/1974 |
| GB | 1 490 671 | 11/1977 |
| GB | 2 271 112 | 6/1994 |
| WO | WO 94/00441 | 1/1994 |
| WO | WO 94/25013 | 11/1994 |
| WO | WO 97/14685 | 4/1997 |
| WO | WO 98/08941 | 3/1998 |
| WO | WO 98/38163 | 9/1998 |
| WO | WO 00/37438 | 6/2000 |
| WO | WO 01/87830 | 11/2001 |
| WO | WO 03/029212 | 4/2003 |
| WO | WO 03/037853 | 5/2003 |

OTHER PUBLICATIONS

Gerrard et al. Neurophychiatric Disease and Treatment 2007, 3(3) 349-364.*
Apfel et al., J. Med. Chem., 43, 2000, pp. 2324-2331.
Bateman et al., Journal of the Chemical Society, 12, 1983, 2903-2912 (abstract only).
Beack et al., J. Org. Chem, 59, 1994, pp. 7410-7413.
Betts et al., Journal of the Chemical Society, 8, 1969, pp. 1178-1184 (abstract only).
Cagniant, et al., Bulletin de la Societe Chimique de France, 1966, pp. 2037-2042.
Chatterjee et al., Biorganic & Medicinal Chemistry Letters, vol. 7, No. 3, 1997, pp. 287-290.

(Continued)

*Primary Examiner* — Yevegeny Valenrod

(57) ABSTRACT

The present invention provides compounds of the structure:

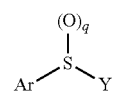

wherein the constituent members are defined herein, including pharmaceutical compositions thereof and methods of treating diseases therewith.

6 Claims, No Drawings

OTHER PUBLICATIONS

Chatterjee et al., Biorganic & Medicinal Chemistry, 6, 1998, pp. 509-522.
Dann, et al., Justus Liebigs Annalen Der Chemie, No. 7, 1973 pp. 1112-1140.
Edgar et al., Journal of Pharmacology and Experimental Therapeutics, 283, 1997, pp. 757-769.
Fujiwara, et al., Journal of Organic Chemistry, vol. 56, No. 5, 1991, pp. 1688-1689.
George et al., Tetrahedron, 24(2), 1968, pp. 1007-1010 (abstract only).
Gracey et al., J. Chem. Soc., 1969, B, pp. 1210-1214.
Gupta et al., Biorganic & Medicinal Chemistry, 10, 2002, pp. 3713-3716.
Hirai et al., Eur. J. Med. Chem., 26, 1991, pp. 143-158.
Janczewski et al., Bull. Acad. Polon. Sci., 13(10), 1965 pp. 669-676 (abstract only).
Janczewski et al., Physica et Chemia, 28, 1977, pp. 1-23, (abstract only).
Janczewski et al., Physica et Chemia, 29-30, 1975, pp. 179-187 (abstract only).
Janczewski et al., Polish Journal of Chemistry, 54 (11-12), 1980, pp. 2161-2173 (abstract only).
Janczewski et al., Polish Journal of Chemistry, 57(7-8-9), 1983, pp. 849-860 (abstract only).
Janczewski et al., Roczniki Chem, 37(10) 1963, pp. 1105-1120 (abstract only).
Janczewski et al., Roczniki Chem. 35, 1961, pp. 585-594 (abstract only).
Janczewski et al., Roczniki Chem., 35, 1961, pp. 601-618 (abstract only).
Janczewski et al., Roczniki Chem., 37, 1963, pp. 635-646 (abstract only).
Janczewski et al., Roczniki Chemii, 40(11/12), 1966, pp. 1919-1931 (abstract only).
Janczewski et al., Roczniki Chemii, 48(2), 1974, pp. 227-241 (abstract only).
Janczewski, Roczniki Chemii, 39(3), 1965, pp. 391-403 (abstract only).
Lisitsyn et al., Zhurnal Organicheskoi Khimii, 16(3), 1980, pp. 629-633 (abstract only).
Lisitsyn et al., Zhurnal Organicheskoi Khimii, 17(11), 1981, pp. 2438-2438 (abstract only).
Macnicol, et al., Journal of the Chemical Society, Perkin Transactions 1, No. 21, 1974, pp. 2493-2496.
Pagani, et al., Il Farmaco, Edizone Scientifica, vol. 33, No. 5, 1978 pp. 332-349.
Panckeri et al., Sleep, 19(8), 1996, pp. 626-631.
Perrone et al., Bioorganic & Medicinal Chemistry, 8, 2000, pp. 873-881.
Perrone et al., European Journal of Medicinal Chemistry, 26(9), 1991, pp. 869-874 (abstract only).
Perrone et al., Il Farmaco, 47(10), 1992, pp. 1285-1291.
Perrone et al., J. Med. Chem., 38, 1995, pp. 942-949.
Rastelli, et al., Biorganic & Medicinal Chemistry, vol. 10, No. 5, 2002, pp. 1437-1450
Rosse et al., Synlett, 4, 2001, pp. 538-540 (abstract only).
Shelton, et al., Sleep, 18(10), 1995, pp. 817-826.
Soczewinski, Roczniki Chemii, 45(5), 1971, pp. 927-929 (abstract only).
Terauchi et al., J. Med. Chem., 40, 1997, pp. 313-321.
Torisawa et al., Tetrahedron Letters, vol. 29, No. 14, 1988, pp. 1729-1732.
Touret et al, Neuroscience Letters, 189, 1995, pp. 43-46.
Vass, et al., Journal of the Chemical Society, Perkin Transactions 2, No. 10, 1997, pp. 2061-2068.
Dostert P. and Jalfre M., *Eur. J. Med. Chem.*, 1974, 9(3), 259-262.
Saenz R.V. and Sowell J.W., *J. Pharm. Sci.*, 1972, 61(6), 978-980.
Portevin, B. et al., *J. Med. Chem.*, 1996, 39, 2379-2391.
Cogniant Bulletin de la Societe Chimique de France, 1950, 28-32 (CAS abstract).

* cited by examiner

US 8,314,155 B2

BICYCLIC AROMATIC SULFINYL DERIVATIVES

REFERENCE TO RELATED APPLICATIONS

The present application is a divisional of U.S. application Ser. No. 11/104,237 filed Apr. 12, 2005, which claims priority to U.S. Provisional Application Ser. No. 60/568,965, filed May 7, 2004 and European Patent Application No. 04290985.3, filed Apr. 13, 2004. The disclosure of each of these applications and patents is hereby incorporated herein by reference in their entireties.

FIELD OF THE INVENTION

The present invention is related to chemical compositions, processes for the preparation thereof and uses of the composition. Particularly, the present invention relates to compositions that include substituted thioacetamides, and their use in the treatment of diseases, such as excessive sleepiness, promotion and/or improvement of wakefulness (preferably improvement of wakefulness in patients with excessive sleepiness associated with narcolepsy, sleep apnea (preferably obstructive sleep apnea/hypopnea) and shift work disorder), treatment of Parkinson's disease, Alzheimer's disease, cerebral ischemia, stroke, eating disorders, attention deficit disorder ("ADD"), attention deficit hyperactivity disorder ("ADHD"), depression, schizophrenia, fatigue (preferably fatigue associated with cancer or neurological diseases, such as multiple sclerosis and chronic fatigue syndrome), stimulation of appetite and weight gain and improvement of cognitive dysfunction.

BACKGROUND OF THE INVENTION

The compounds disclosed herein are related to the biological and chemical analogs of modafinil. Modafinil, $C_{15}H_{15}NO_2S$, also known as 2-(benzhydrylsulfinyl)acetamide, or 2-[(diphenylmethyl) sulfinyl]acetamide, a synthetic acetamide derivative with wake-promoting activity, has been described in French Patent No. 78 05 510 and in U.S. Pat. No. 4,177,290 ("the '290 patent"). It has been approved by the United States Food and Drug Administration for use in the treatment of excessive daytime sleepiness associated with narcolepsy. Methods for preparing modafinil and several derivatives are described in the '290 patent. The levorotatory isomer of modafinil, along with additional modafinil derivatives are described in U.S. Pat. No. 4,927,855, and are reported to be useful for treatment of hypersomnia, depression, Alzheimer's disease and to have activity towards the symptoms of dementia and loss of memory, especially in the elderly.

Modafinil has also been described as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas and disorders of central origin (U.S. Pat. No. 5,612,379). In addition, modafinil may be used in the treatment of eating disorders, and to promote weight gain or stimulate appetite in humans or animals (U.S. Pat. No. 6,455,588), and in the treatment of attention deficit hyperactivity disorder (U.S. Pat. No. 6,346,548), and fatigue, especially fatigue associated with multiple sclerosis (U.S. Pat. No. 6,488,164). U.S. Pat. No. 4,066,686 describes various benzhydrylsulphinyl derivatives as being useful in therapy for treating disturbances of the central nervous system.

Several published patent applications describe derivative forms of modafinil and the use of modafinil derivatives in the treatment of various disorders. For example, PCT publication WO 99/25329 describes various substituted phenyl analogs of modafinil as being useful for treating drug-induced sleepiness, especially sleepiness associated with administration of morphine to cancer patients. U.S. Pat. No. 5,719,168 and PCT Publication No. 95/01171 describes modafinil derivatives that are useful for modifying feeding behavior. PCT Publication No. 02/10125 describes several modafinil derivatives of modafinil, along with various polymorphic forms of modafinil.

Additional publications describing modafinil derivatives include U.S. Pat. No. 6,492,396, and PCT Publ. No. WO 02/10125.

Terauchi, H, et al. described nicotinamide derivatives useful as ATP-ase inhibitors (Terauchi, H, et al, *J. Med. Chem.*, 1997, 40, 313-321). In particular, several N-alkyl substituted 2-(Benzhydrylsulfinyl)nicotinamides are described.

U.S. Pat. Nos. 4,980,372 and 4,935,240 describe benzoylaminophenoxybutanoic acid derivatives. In particular, sulfide derivatives of modafinil containing a phenyl and substituted phenyl linker between the sulfide and carbonyl, and a substituted aryl in the terminal amide position, are disclosed.

Other modafinil derivatives have been disclosed wherein the terminal phenyl groups are constrained by a linking group. For example, in U.S. Pat. No. 5,563,169, certain xanthenyl and thiaxanthenyl derivatives having a substituted aryl in the terminal amide position are reported.

Other xanthenyl and thiaxanthenyl derivatives are disclosed in Annis, I; Barany, G. *Pept. Proc. Am. Pept. Symp.* $15^{th}$ (Meeting Date 1997) 343-344, 1999 (preparation of a xanthenyl derivative of Ellman's Reagent, useful as a reagent in peptide synthesis); Han, Y.; Barany, G. *J. Org. Chem.*, 1997, 62, 3841-3848 (preparation of S-xanthenyl protected cysteine derivatives, useful as a reagent in peptide synthesis); and El-Sakka, I. A., et al. *Arch. Pharm.* (Weinheim), 1994, 327, 133-135 (thiaxanthenol derivatives of thioglycolic acid).

Thus, there is a need for novel classes of compounds that possess the beneficial properties similar to that of modafinil. It has been discovered that a class of compounds, referred to herein as substituted thioacetamides, are useful as agents for treating or preventing various diseases or disorders disclosed herein.

SUMMARY OF THE INVENTION

The present invention in one aspect is directed to novel compounds which are useful in the treatment of diseases, such as excessive sleepiness, promotion and/or improvement of wakefulness (preferably improvement of wakefulness in patients with excessive sleepiness associated with narcolepsy, sleep apnea (preferably obstructive sleep apnea/hypopnea) and shift work disorder), treatment of Parkinson's disease, Alzheimer's disease, cerebral ischemia, stroke, eating disorders, attention deficit disorder ("ADD"), attention deficit hyperactivity disorder ("ADHD"), depression, schizophrenia, fatigue (preferably fatigue associated with cancer or neurological diseases, such as multiple sclerosis and chronic fatigue syndrome), stimulation of appetite and weight gain and improvement of cognitive dysfunction.

These compounds have the structure:

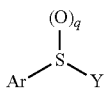

and its stereoisomeric forms, mixtures of stereoisomeric forms, or pharmaceutically acceptable salt forms thereof, wherein the constituent members are defined infra.

In another aspect, the present invention is directed to a pharmaceutical composition which comprises a pharmaceutically acceptable carrier and a therapeutically effective amount of a compound of the present invention.

In yet another aspect, the present invention is directed to methods of preventing or treating the diseases or disorders disclosed herein.

DETAILED DESCRIPTION OF THE INVENTION

In one aspect of the present invention there are provided compounds of formula (A) for the utilities provided herein:

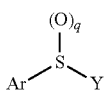

(A)

wherein
Ar is

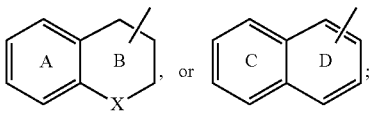

wherein X is a bond, $CH_2$, O, $S(O)_y$, or $NR^{10}$;
rings A, C, and D are optionally substituted with one to three groups selected from F, Cl, Br, I, $OR^{21}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, and $S(O)_yR^{22}$;
ring B is optionally substituted with one to three groups selected from $C_1$-$C_6$ alkyl, phenyl, and 5-6 membered heteroaryl;
Y is $C_1$-$C_9$ alkylene-$R^1$, wherein one or two carbon atoms can be replaced by one or two O, $NR^{10}$, or $S(O)_y$ groups, or a carbon atom can be replaced by a $C_6$-$C_{10}$ arylene, 5-10 membered heteroarylene, $C_3$-$C_6$ cycloalkylene, or 3-6 membered heterocycloalkylene group; $C_2$-$C_6$ alkenylene-$R^1$; or $C_2$-$C_6$ alkynylene-$R^1$; wherein said alkylene, alkenylene, alkynylene, arylene, heteroarylene, cycloalkylene, and heterocycloalkylene groups are optionally substituted with one to three $R^{20}$ groups;
$R^1$ is H, $NR^{12}R^{13}$, $NR^{21}C(=O)R^{14}$, $C(=O)R^{15}$, COOH, $CO_2R^{14}$, $OC(=O)R^{11}$, $C(=O)NR^{12}R^{13}$, $C(=O)NR^{21}OR^{14}$, $C(=N)NR^{12}R^{13}$, $NR^{21}S(O)_2R^{11}$, $S(O)_2NR^{12}R^{13}$, $NR^{21}S(O)_2NR^{12}R^{13}$, or $PO(OR^{21})_2$;
$R^{10}$ and $R^{10A}$ are each independently selected from H, $C_1$-$C_6$ alkyl, $C_6$-$C_{10}$ aryl, $C(=O)R^{15}$, and $S(O)_yR^{14}$; wherein said alkyl and aryl groups are optionally substituted with one to three $R^{20}$ groups;

$R^{11}$ at each occurrence is independently selected from H, $C_1$-$C_6$ alkyl, and $C_6$-$C_{10}$ aryl; wherein said alkyl and aryl groups are optionally substituted with one to three $R^{20}$ groups;
$R^{12}$ and $R^{13}$ at each occurrence are each independently selected from H, $C_1$-$C_6$ alkyl, and $C_6$-$C_{10}$ aryl, or $R^{12}$ and $R^{13}$, together with the nitrogen to which they are attached, form a 3-7 membered heterocycloalkyl ring;
wherein said alkyl and aryl groups and heterocycloalkyl ring are optionally substituted with one to three $R^{20}$ groups;
$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;
$R^{15}$ at each occurrence is independently selected from $C_1$-$C_6$ alkyl, $C_6$-$C_{10}$ aryl, arylalkyl, and heteroaryl; wherein said alkyl, aryl, arylalkyl, and heteroaryl groups are optionally substituted with one to three $R^{20}$ groups;
$R^{20}$ at each occurrence is independently selected from F, Cl, Br, I, $OR^{21}$, $OR^{25}$, $O(C_1$-$C_4$ alkylene)$OR^{21}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;
$R^{21}$ at each occurrence is independently selected from H and $C_1$-$C_6$ alkyl;
$R^{22}$ at each occurrence is independently selected from H, $C_1$-$C_6$ alkyl and $C_6$-$C_{10}$ aryl;
$R^{23}$ and $R^{24}$ at each occurrence are each independently selected from H, $C_1$-$C_6$alkyl, and $C_6$-$C_{10}$ aryl, or $R^{23}$ and $R^{24}$, together with the nitrogen to which they are attached, form a 3-7 membered heterocycloalkyl ring;
$R^{25}$ at each occurrence is independently the residue of an amino acid after the hydroxyl group of the carboxyl group is removed;
q is 0, 1, or 2;
y is 0, 1, or 2;
and the stereoisomeric forms, mixtures of stereoisomeric forms or pharmaceutically acceptable salts forms thereof.

In an additional aspect of the present invention there are provided compounds of formula (I):

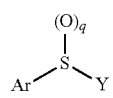

(I)

wherein
Ar is

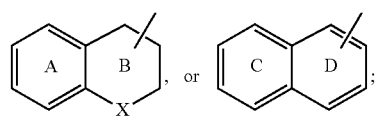

wherein X is a bond, $CH_2$, O, $S(O)_y$, or $NR^{10}$;
rings A, C, and D are optionally substituted with one to three groups selected from F, Cl, Br, I, $OR^{21}$, $OR^{25}$, $NR^{23}R^{24}$, NHOH, $NO_2$, CN, $CF_3$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $C(=O)R^{22}$, $CO_2R^2$, $OC(=O)R^{22}$, $C(=O)NR^{22}R^{21}$, $NR^{21}C(=O)R^{22}$, $NR^{21}CO_2R^{22}$, $OC(=O)NR^{23}R^{24}$, $NR^{21}C(=S)R^{22}$ and $S(O)_yR^{22}$;

ring B is optionally substituted with one to three groups selected from $C_1$-$C_6$ alkyl, phenyl, and 5-6 membered heteroaryl;

Y is $(C_1$-$C_6$ alkylene$)$-$R^1$; or $(C_1$-$C_4$ alkylene$)_m$-Z-$(C_1$-$C_4$ alkylene$)_n$-$R^1$;

wherein said alkylene groups are optionally substituted with one to three $R^{20}$ groups;

Z is O, $NR^{10A}$, $S(O)_y$, $CR^{21}=CR^{21}$, $C=C(R^{21})_2$, $C≡C$, $C_6$-$C_{10}$arylene, 5-10 membered heteroarylene, $C_3$-$C_6$ cycloalkylene, or 3-6 membered heterocycloalkylene; wherein said arylene, heteroarylene, cycloalkylene, and heterocycloalkylene groups are optionally substituted with one to three $R^{20}$ groups;

$R^1$ is $NR^{12}R^{13}$, $NR^{21}C(=O)R^{14}$, $C(=O)R^{15}$, COOH, $CO_2R^{14}$, $OC(=O)R^{11}$, $C(=O)NR^{12}R^{13}$, $C(=N)NR^{12}R^{13}$, $OC(=O)NR^{12}R^{13}$, $NR^{21}S(O)_2R^{11}$, $S(O)_2NR^{12}R^{13}$, $NR^{21}C(=O)NR^{12}R^{13}$, $NR^{21}S(O)_2NR^{12}R^{13}$, or $PO(OR^{21})_2$;

$R^{10}$ and $R^{10A}$ are each independently selected from H, $C_1$-$C_6$ alkyl, $C_6$-$C_{10}$ aryl, $C(=O)R^{15}$, and $S(O)_yR^{14}$; wherein said alkyl and aryl groups are optionally substituted with one to three $R^{20}$ groups;

$R^{11}$ at each occurrence is independently selected from H, $C_1$-$C_6$ alkyl, and $C_6$-$C_{10}$ aryl; wherein said alkyl and aryl groups are optionally substituted with one to three $R^{20}$ groups;

$R^{12}$ and $R^{13}$ at each occurrence are each independently selected from H, $C_1$-$C_6$ alkyl, and $C_6$-$C_{10}$ aryl, or $R^{12}$ and $R^{13}$, together with the nitrogen to which they are attached, form a 3-7 membered heterocycloalkyl ring;

wherein said alkyl and aryl groups and heterocycloalkyl ring are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;

$R^{15}$ at each occurrence is independently selected from $C_1$-$C_6$ alkyl, $C_6$-$C_{10}$ aryl, arylalkyl, and heteroaryl; wherein said alkyl, aryl, arylalkyl, and heteroaryl groups are optionally substituted with one to three $R^{20}$ groups;

$R^{20}$ at each occurrence is independently selected from F, Cl, Br, I, $OR^{21}$, $OR^{25}$, $O(C_1$-$C_4$ alkylene$)OR^{21}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from H, $C_1$-$C_6$ alkyl; and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocycloalkyl ring;

$R^{25}$ at each occurrence is independently the residue of an amino acid after the hydroxyl group of the carboxyl group is removed;

m is 0 or 1;
n is 0 or 1;
q is 0, 1, or 2;
y is 0, 1, or 2;

with the following proviso's:
1. when X is $CH_2$ or O, and Y is $C_1$-$C_6$ alkyl-$C(=O)NR^{12}R^{13}$, then q must be 1 or 2;
2. when Ar is naphthyl, and Y is $C_1$-$C_6$ alkyl-$C(=O)NR^{12}R^{13}$, then naphthyl cannot be substituted with phenyl or heteroaryl, and $R^{12}$ and $R^{13}$ cannot both be H;
3. when Ar is naphthyl and Y is $C_1$-$C_4$ alkyl-COOR, wherein R is H or $C_1$-$C_6$ alkyl, then q must be 1 or 2;
4. when Ar is indane, then Y cannot be -triazolyl-$C(=O)NR^{12}R^{13}$;

and the stereoisomeric forms, mixtures of stereoisomeric forms or pharmaceutically acceptable salts forms thereof.

In additional embodiments of compounds of formula (I), when Ar is naphthyl, and Y is $C_1$-$C_6$ alkyl-$C(=O)NR^{12}R^{13}$, then naphthyl cannot be substituted with phenyl or heteroaryl, and one of $R^{12}$ and $R^{13}$ must be $C_1$-$C_6$ alkyl, or $C_1$-$C_6$ alkyl substituted with at least one $OR^{21}$ or $C(=O)NR^{23}R^{24}$ group, or $R^{12}$ and $R^{13}$, together with the nitrogen to which they are attached, form a pyrrolidinyl, piperidinyl, or piperazinyl ring substituted with $OR^{21}$, $C(=O)N(R^{21})_2$, or $C(=O)R^{21}$. In another aspect, when Ar is naphthyl and Y is $C_1$-$C_6$ alkyl-$C(=O)NR^{12}R^{13}$, then the naphthyl must be unsubstituted. In an additional aspect, when Ar is naphthyl and Y is $C_1$-$C_6$ alkyl-$C(=O)NR^{12}R^{13}$, then one of $R^{12}$ and $R^{13}$ must be $C_1$-$C_6$ alkyl, or $C_1$-$C_6$ alkyl substituted with at least one $OR^{21}$ or $C(=O)NR^{23}R^{24}$ group. In an additional aspect, when Ar is naphthyl, then Y cannot be $C_1$-$C_6$ alkyl-COOR, wherein R is H or $C_1$-$C_6$ alkyl.

In yet another embodiment of the present invention there are provided compounds of formula (II):

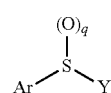

(II)

wherein
Ar is

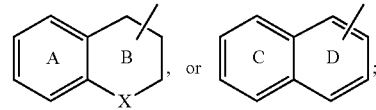

wherein X is a bond, $CH_2$, O, $S(O)_y$, or $NR^{10}$; rings A, C, and D are optionally substituted with one to three groups selected from F, Cl, Br, I, $OR^{21}$, $OR^{21}$, $NR^{21}R^{24}$, NHOH, $NO_2$, CN, $C_1$-$C_6$ alkyl, and $C(=O)R^{22}$;

ring B is optionally substituted with one to three groups selected from $C_1$-$C_4$ alkyl, and phenyl;

Y is $(C_1$-$C_6$ alkylene$)$-$R^1$;

wherein said alkylene group is optionally substituted with one to three $R^{20}$ groups;

$R^1$ is $NR^{12}R^{13}$, $NR^{21}C(=O)R^{14}$, $C(=O)R^{15}$, COOH, $CO_2R^{14}$, $OC(=O)R^{11}$, $C(=O)NR^{12}R^{13}$, $C(=O)NR^{21}OR^{14}$, $C(=N)NR^{12}R^{13}$, $OC(=O)NR^{12}R^{13}$, $NR^{21}S(O)_2R^{11}$, $S(O)_2NR^{12}R^{13}$, $NR^{21}C(=O)NR^{12}R^{13}$, $NR^{21}S(O)_2NR^{12}R^{13}$, or $PO(OR^{21})_2$;

$R^{10}$ is independently selected from H, $C_1$-$C_6$ alkyl, $C(=O)R^{15}$, and $S(O)_yR^{14}$; wherein said alkyl group is optionally substituted with one to three $R^{20}$ groups;

$R^{11}$ at each occurrence is independently selected from H, and $C_1$-$C_6$ alkyl; wherein said alkyl and aryl groups are optionally substituted with one to three $R^{20}$ groups;

$R^{12}$ and $R^{13}$ at each occurrence are each independently selected from H and $C_1$-$C_6$ alkyl, or $R^{12}$ and $R^3$, together with the nitrogen to which they are attached, form a 5-6 membered heterocycloalkyl;
wherein said alkyl and heterocycloalkyl groups are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;

$R^{15}$ at each occurrence is independently selected from $C_1$-$C_6$ alkyl, $C_6$-$C_{10}$ aryl, arylalkyl, and heteroaryl; wherein said alkyl, aryl, arylalkyl, and heteroaryl groups are optionally substituted with one to three $R^{20}$ groups;

$R^{20}$ at each occurrence is independently selected from F, Cl, Br, I, $OR^{21}$, $OR^{25}$, $O(C_1$-$C_4$ alkylene)$OR^{21}$, $NR^{23}R^{24}$, NHOH, $NO_2$, CN, $CF_3$, phenyl, benzyl, 5-6 membered heteroaryl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from $C_1$-$C_6$ alkyl, and phenyl;

$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

q is 0, 1, or 2;

y is 0, 1, or 2;

with the following proviso's:
1. when X is $CH_2$ or O, and Y is $C_1$-$C_6$ alkyl-$C(=O)NR^{12}R^{13}$, then q must be 1 or 2;
2. when Ar is naphthyl, and Y is $C_1$-$C_6$ alkyl-$C(=O)NR^{12}R^{13}$, then $R^{12}$ and $R^{13}$ cannot both be H;
3. when Ar is naphthyl and Y is $C_1$-$C_6$ alkyl-COOR, wherein R is H or $C_1$-$C_6$ alkyl, then q must be 1 or 2;

and the stereoisomeric forms, mixtures of stereoisomeric forms or pharmaceutically acceptable salts forms thereof.

In additional embodiments of compounds of formula (II), when Ar is naphthyl, and Y is $C_1$-$C_6$ alkyl-$C(=O)NR^{12}R^{13}$, then one of $R^{12}$ and $R^{13}$ must be $C_1$-$C_6$ alkyl, or $C_1$-$C_6$ alkyl substituted with at least one $OR^{21}$ or $C(=O)NR^{12}R^{13}$ group, or $R^{12}$ and $R^{13}$, together with the nitrogen to which they are attached, form a pyrrolidinyl, piperidinyl, or piperazinyl ring substituted with $OR^{21}$, $C(=O)N(R^{21})_2$, or $C(=O)R^{21}$. In another aspect, when Ar is naphthyl and Y is $C_1$-$C_6$ alkyl-$C(=O)NR^{12}R^{13}$, then the naphthyl must be unsubstituted. In an additional aspect, when Ar is naphthyl and Y is $C_1$-$C_6$ alkyl-$C(=O)NR^{12}R^{13}$, then one of $R^{12}$ and $R^{13}$ must be $C_1$-$C_6$ alkyl, or $C_1$-$C_6$ alkyl substituted with at least one $OR^{21}$ or $C(=O)NR^{23}R^{24}$ group. In an additional aspect, when Ar is naphthyl, then Y cannot be $C_1$-$C_6$ alkyl-COOR, wherein R is H or $C_1$-$C_6$ alkyl.

In yet another embodiment of the present invention there are provided compounds of formula (III):

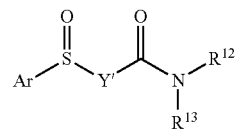

(III)

wherein
Ar is

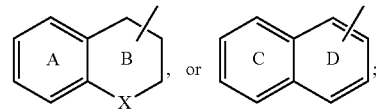

wherein X is a bond, $CH_2$, O, $S(O)_y$, or $NR^{10}$;

rings A, C, and D are optionally substituted with one to three groups selected from F, Cl, Br, I, $OR^{21}$, $OR^{25}$, $NR^{23}R^{24}$, NHOH, $NO_2$, CN, $C_1$-$C_6$ alkyl, and $C(=O)R^{22}$;

ring B is optionally substituted with one to three groups selected from $C_1$-$C_4$ alkyl, and phenyl;

Y' is $C_1$-$C_4$alkylene;

$R^{10}$ is independently selected from H, $C_1$-$C_6$ alkyl, $C(=O)R^{15}$, and $S(O)_yR^{14}$;

$R^{12}$ and $R^{13}$ at each occurrence are each independently selected from H and $C_1$-$C_6$ alkyl, or $R^{12}$ and $R^3$, together with the nitrogen to which they are attached, form a 5-6 membered heterocycloalkyl;
wherein said alkyl and heterocycloalkyl groups are optionally substituted with one to three $R^{20}$ groups;

$R^{14}$ at each occurrence is independently $C_1$-$C_6$ alkyl; wherein said alkyl is optionally substituted with one to three $R^{20}$ groups;

$R^{15}$ at each occurrence is independently selected from $C_1$-$C_6$ alkyl, phenyl, and benzyl; wherein said alkyl, phenyl and benzyl groups are optionally substituted with one to three $R^{20}$ groups;

$R^{20}$ at each occurrence is independently selected from F, Cl, Br, I, $OR^{21}OR^{25}$, $O(C_1$-$C_4$ alkylene)$OR^{21}$, $NR^{23}R^{24}$, NHOH, $NO_2$, CN, $CF_3$, phenyl, benzyl, 5-6 membered heteroaryl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from $C_1$-$C_6$ alkyl, and phenyl;

$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

q is 0, 1, or 2;

y is 0, 1, or 2;

with the proviso that when Ar is naphthyl, then $R^{12}$ and $R^{13}$ cannot both be H;

and the stereoisomeric forms, mixtures of stereoisomeric forms or pharmaceutically acceptable salts forms thereof.

In additional embodiments of compounds of formula (III), when Ar is naphthyl, then one of $R^{12}$ and $R^{13}$ must be $C_1$-$C_6$ alkyl, or $C_1$-$C_6$ alkyl substituted with at least one $OR^{21}$ or $C(=O)NR^{23}R^{24}$ group, or $R^{12}$ and $R^{13}$, together with the nitrogen to which they are attached, form a pyrrolidinyl, piperidinyl, or piperazinyl ring substituted with $OR^{21}$, $C(=O)N(R^{21})_2$, or $C(=O)R^{21}$. In another aspect, when Ar is naphthyl, then the naphthyl must be unsubstituted.

In yet another embodiment of the present invention, there are provided compounds of formula (IV):

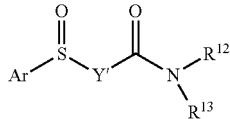
(IV)

wherein
Ar is

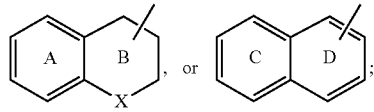

wherein X is a bond, $CH_2$, O, S, or S(O);
rings A, C, and D are optionally substituted with one to three groups selected from F, Cl, Br, I, $OR^{21}$, $OR^{25}$, $NR^{23}R^{24}$, NHOH, $NO_2$, CN, $C_1$-$C_6$ alkyl, and $C(=O)R^{22}$;
ring B is optionally substituted with one to three groups selected from $C_1$-$C_4$ alkyl, and phenyl;
Y' is $C_1$-$C_4$ alkylene, wherein said alkylene group is optionally substituted with an $R^{20}$ group;
$R^{12}$ and $R^{13}$ at each occurrence are each independently selected from H, $C_1$-$C_6$ alkyl, wherein said alkyl group can optionally be substituted with one or two CN, $OR^{21}$, $O(CH_2)_{1-4}OR^{21}$, $C(=O)N(R^{21})_2$, or pyridyl groups, or $R^{12}$ and $R^{13}$, together with the nitrogen to which they are attached, form a pyrrolidinyl, piperidinyl, or piperazinyl ring, optionally substituted with $OR^{21}$, $C(=O)N(R^{21})_2$, or $C(=O)R^{21}$;
$R^{20}$ at each occurrence is independently selected from F, Cl, Br, I, $OR^{21}$, $OR^{25}$, $NR^{23}R^{24}$, NHOH, $NO_2$, CN, or $CF_3$;
$R^{21}$ at each occurrence is independently selected from H and $C_1$-$C_6$ alkyl;
$R^{22}$ at each occurrence is independently selected from $C_1$-$C_6$ alkyl, and phenyl;
$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;
$R^{25}$ at each occurrence is independently the residue of an amino acid after the hydroxyl group of the carboxyl group is removed;
with the proviso that when Ar is naphthyl, then $R^{12}$ and $R^{13}$ cannot both be H;
and the stereoisomeric forms, mixtures of stereoisomeric forms or pharmaceutically acceptable salts forms thereof.

In additional embodiments of compounds of formula (IV), when Ar is naphthyl, then one of $R^{12}$ and $R^{13}$ must be $C_1$-$C_6$ alkyl, or $C_1$-$C_6$ alkyl substituted with at least one $OR^{21}$ or $C(=O)NR^{23}R^{24}$ group, or $R^{12}$ and $R^{13}$, together with the nitrogen to which they are attached, form a pyrrolidinyl, piperidinyl, or piperazinyl ring substituted with $OR^{21}$, $C(=O)N(R^{21})_2$, or $C(=O)R^{21}$. In another aspect, when Ar is naphthyl, then the naphthyl must be unsubstituted.

In one aspect, there are included compounds of formula (IV) wherein X is a bond; q is 1; Y' is ($C_1$-$C_2$ alkylene), or Y' is $CH_2$, or Y' is $CH_2CH_2$; $R^{12}$ and $R^{13}$ at each occurrence are each independently selected from H, $C_1$-$C_6$ alkyl, optionally substituted with a CN, $OR^{21}$, $O(CH_2)_{1-4}OR^{21}$ group, or $R^{12}$ and $R^{13}$, together with the nitrogen to which they are attached, form a pyrrolidinyl, piperidinyl, or piperazinyl ring, optionally substituted with $OR^{21}$, $C(=O)N(R^{21})_2$, or $C(=O)R^{21}$ group, or they form a pyrrolidinyl ring, optionally substituted with $C(=O)N(R^2)_2$; a piperidinyl ring, optionally substituted with $OR^{21}$; or a piperazinyl ring, optionally substituted with $C(=O)R^{21}$.

In another aspect, there are provided compounds of formula (IV) wherein X is $CH_2$; q is 1; Y' is $CH_2$; $R^{12}$ and $R^{13}$ at each occurrence are each independently selected from H, $C_1$-$C_6$ alkyl, or $R^{12}$ and $R^{13}$, together with the nitrogen to which they are attached, form a pyrrolidinyl ring.

In a further aspect, there are provided compounds of formula (IV) wherein X is O; q is 1; Y' is $CH_2$; $R^{12}$ and $R^{13}$ at each occurrence are each independently selected from H, $C_1$-$C_6$ alkyl, wherein said alkyl group can optionally be substituted with pyridyl, or $R^{12}$ and $R^{13}$, together with the nitrogen to which they are attached, form a pyrrolidinyl ring.

In yet another aspect, there are provided compounds of formula (IV) wherein X is S or S=O; q is 1; Y' is $CH_2$; $R^{12}$ and $R^{13}$ at each occurrence are each independently selected from H, $C_1$-$C_6$ alkyl.

In a further aspect, there are provided compounds of formula (IV) wherein Ar is naphthyl; q is 1, Y' is $CH_2$; $R^{12}$ and $R^{13}$ at each occurrence are each independently selected from $C_1$-$C_6$ alkyl, wherein said alkyl group can optionally be substituted with $OR^{21}$, or one or two $C(=O)N(R^{21})_2$ groups, or $R^{12}$ and $R^{13}$, together with the nitrogen to which they are attached, form a pyrrolidinyl ring, optionally substituted with $C(=O)N(R^2)_2$.

In a further embodiment of the present invention there are provided compounds of formula (V):

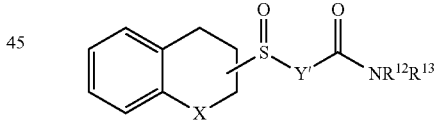
(V)

wherein the phenylene ring is optionally substituted with one to three groups selected from F, Cl, Br, I, $OR^{21}$, $OR^{25}$, $NR^{23}R^{24}$, NHOH, $NO_2$, CN, $C_1$-$C_6$ alkyl, and $C(=O)R^{22}$;
X is a bond, $CH_2$, O, S, or S(O);
Y' is $C_1$-$C_4$ alkylene, wherein said alkylene group is optionally substituted with an $R^{20}$ group;
$R^{12}$ and $R^{13}$ at each occurrence are each independently selected from H, $C_1$-$C_6$ alkyl, wherein said alkyl group can optionally be substituted with one or two CN, $OR^{21}$, $O(CH_2)_{1-4}OR^{21}$, $C(=O)N(R^{21})_2$, or pyridyl groups, or $R^{12}$ and $R^{13}$, together with the nitrogen to which they are attached, form a pyrrolidinyl, piperidinyl, or piperazinyl ring, optionally substituted with $OR^{21}$, $C(=O)N(R^{21})_2$, or $C(=O)R^{21}$;
$R^{20}$ at each occurrence is independently selected from F, Cl, Br, I, $OR^{21}$, $OR^{25}$, $NR^{23}R^{24}$, NHOH, $NO_2$, CN, or $CF_3$;
$R^{21}$ at each occurrence is independently selected from H and $C_1$-$C_6$ alkyl;

$R^{22}$ at each occurrence is independently selected from $C_1$-$C_6$ alkyl, and phenyl;

$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

and the stereoisomeric forms, mixtures of stereoisomeric forms or pharmaceutically acceptable salts forms thereof.

In an additional embodiment of the present invention there are provided compounds of formula (VI):

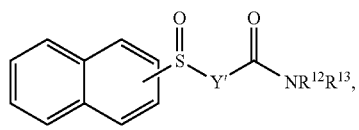

(VI)

wherein the naphthyl ring is optionally substituted with one to three groups selected from F, Cl, Br, I, $OR^{21}$, $OR^{25}$, $NR^{23}R^{24}$, NHOH, $NO_2$, CN, $C_1$-$C_6$ alkyl, and $C(=O)R^{22}$;

Y' is $C_1$-$C_4$ alkylene, wherein said alkylene group is optionally substituted with an $R^{20}$ group;

$R^{12}$ and $R^{13}$ at each occurrence are each independently selected from H, $C_1$-$C_6$ alkyl, wherein said alkyl group can optionally be substituted with one $OR^{21}$ or $C(=O)N(R^{21})_2$ group, or $R^{12}$ and $R^{13}$, together with the nitrogen to which they are attached, form a pyrrolidinyl, piperidinyl, or piperazinyl ring substituted with $OR^{21}$, $C(=O)N(R^{21})_2$, or $C(=O)R^{21}$; provided that $R^{12}$ and $R^{13}$ cannot both be H;

$R^{20}$ at each occurrence is independently selected from F, Cl, Br, I, $OR^{21}$, $OR^{25}$, $NR^{23}R^{24}$, NHOH, $NO_2$, CN, or $CF_3$;

$R^{21}$ at each occurrence is independently selected from H and $C_1$-$C_6$ alkyl;

$R^{22}$ at each occurrence is independently selected from $C_1$-$C_6$ alkyl, and phenyl;

$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

with the proviso that when Ar is naphthyl, then $R^{12}$ and $R^{13}$ cannot both be H; and the stereoisomeric forms, mixtures of stereoisomeric forms or pharmaceutically acceptable salts forms thereof.

In additional embodiments of compounds of formula (VI), one of $R^{12}$ and $R^{13}$ must be $C_1$-$C_6$ alkyl, or $C_1$-$C_6$ alkyl substituted with at least one $OR^{21}$ or $C(=O)NR^{23}R^{24}$ group. In another aspect, the naphthyl must be unsubstituted.

In a further aspect, there are provided compounds of formula (VI) having a structure of formula (VII):

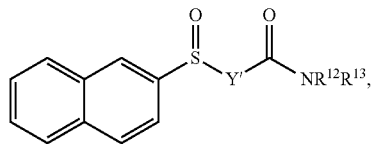

(VII)

wherein Y', $R^{12}$, and $R^{13}$ are as defined for compounds of formula (VI), and the stereoisomeric forms, mixtures of stereoisomeric forms or pharmaceutically acceptable salts forms thereof.

In additional embodiments of compounds of formula (VII), one of $R^{12}$ and $R^{13}$ must be $C_1$-$C_6$ alkyl, or $C_1$-$C_6$ alkyl substituted with at least one $OR^{21}$ or $C(=O)NR^{23}R^{24}$ group.

A further aspect of the present invention includes compounds of formula (A) wherein Y is $C_1$-$C_6$ alkyl substituted with halogen, $CF_3$, or $OR^{21}$; $C_1$-$C_6$ alkylene-$R^1$; $C_1$-$C_4$ alkylene-$Z^1$-$C_1$-$C_4$ alkylene-$R^2$; or $C_1$-$C_4$ alkylene-$Z^2$-$C_1$-$C_4$ alkylene-$R^{2A}$; wherein $R^2$ and $R^{2A}$ are the same as $R^1$ less the H moiety, and wherein said alkylene groups are optionally substituted with one to three $C_1$-$C_6$ alkyl groups; $Z^1$ is $CR^{21}=CR^{21}$, $C=C(R^{21})_2$, $C\equiv C$, or phenyl; $Z^2$ is O, $NR^{10A}$, or $S(O)_y$; $R^1$ is selected from $NR^{21}C(=O)R^{14}$, $C(=O)R^{14}$, $CO_2R^{11}$, $OC(=O)R^{11}$, and $C(=O)NR^{12}R^{13}$. In other aspects, Y is $C_1$-$C_6$ alkylene-$R^1$, or $C_1$-$C_4$ alkylene-$Z^1$-$C_1$-$C_4$ alkylene-$R^2$. In additional aspects, Y is $C_1$-$C_6$ alkylene-$R^1$. In other aspects, $R^1$ is selected from $NR^{12}R^{13}$, wherein $R^{12}$ and $R^{13}$ are each independently selected from H and $C_1$-$C_6$ alkyl, or $R^{12}$ and $R^{13}$, together with the nitrogen to which they are attached, form a pyrrolidinyl, piperidinyl, or morpholinyl; $NR^{21}C(=O)R^{14}$; $C(=O)NR^{12}R^{13}$; $C(=N)NR^{12}R^{13}$; and $NR^{21}C(=O)NR^{12}R^{13}$. In additional aspects, $R^1$ is $C(=O)NR^{12}R^{13}$.

In additional aspects of the present invention there are included compounds of any of the preceding formulas wherein q is 1 or 2. In certain aspects, q is 0. In other aspects q is 1. In further aspects, q is 2.

In certain aspects of the present invention, there are included compounds of any of the preceding formulas wherein q have any of the values of the previous embodiments and Ar is selected as follows. In one aspect, Ar is

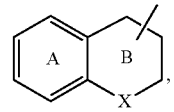

particularly those where X is a bond, or X is $CH_2$, or X is O, or X is S, or X is S=O), or X is $NR^{10}$. Other aspects include compounds where Ar is naphthyl. In still further aspects, the present invention includes compounds wherein q and Ar have any values of their previous embodiments.

Other aspects of the present invention include compounds of any of the preceding formulas wherein Ar and q can be any moieties of the previous embodiments, and Y is $C_1$-$C_6$ alkylene-$R^1$, particularly those where Y is $C_1$-$C_4$ alkylene-$R^1$, or Y is $CH_2$—$R^1$, or Y is $CH_2CH_2$—$R^1$.

Additional aspects of the present invention include compounds of any of the preceding formulas wherein Ar, q, and Y can be any moieties of the previous embodiments, and Y is ($C_1$-$C_4$ alkylene)$_m$-$Z^1$-($C_1$-$C_4$ alkylene)$_n$-$R^1$, wherein $Z^1$ is $CR^{21}=CR^{21}$, $C=C(R^{22})$, $C\equiv C$, $C_6$-$C_{10}$ arylene, 5-10 membered heteroarylene, $C_3$-$C_6$ cycloalkylene, or 3-6 membered heterocycloalkylene, particularly those where Y is $C_1$-$C_4$ alkylene-$Z^1$-$R^1$, or Y is $Z^1$-$C_1$-$C_4$ alkylene-$R^1$, or Y is $C_1$-$C_4$ alkylene-$Z^1$-$C_1$-$C_4$ alkylene-$R^1$. In other aspects, $Z^1$ is $CR^{21}=CR^{21}$, $C=C(R^{22})$, $C\equiv C$, or phenylene, or more particularly where $Z^1$ is $CR^{21}=CR^{21}$ or $Z^1$ is phenylene. Other aspects include compounds where $Z^1$ is $CR^{21}=CR^{21}$, or $C\equiv C$.

Further aspects of the present invention include compounds of any of the preceding formulas wherein Ar, q, and Y can be any moieties of the previous embodiments, and Y is ($C_1$-$C_4$ alkylene)$_m$-$Z^2$-($C_1$-$C_4$ alkylene)$_n$-$R^1$, wherein $Z^2$ is O, $NR^{10A}$, or $S(O)_y$, particularly those where $Z^2$ is O. In certain aspects, Y is $C_1$-$C_4$ alkylene-$Z^2$-$C_1$-$C_4$ alkylene-$R^1$, or Y is $C_1$-$C_4$ alkylene-$Z^2$-$R^1$.

Further aspects of the present invention include compounds of any of the preceding formulas wherein Ar, Y, $Z^1$, and $Z^2$, and q can be any moieties of the previous embodiments, and $R^1$ can be any moiety selected from the following enumerated paragraphs:

1. $NR^{12}R^{13}$.
2. $NR^{21}C(=O)R^{14}$.
3. $C(=O)R^{15}$.
4. COOH or $CO_2R^{14}$.
5. $OC(=O)R^{11}$.
6. $C(=O)NR^{12}R^{13}$.
7. $C(=O)NR^{21}OR^{14}$.
8. $C(=N)NR^{12}R^{13}$.
9. $OC(=O)NR^{12}R^{13}$.
10. $NR^{21}S(O)_2R^{11}$.
11. $S(O)_2NR^{12}R^{13}$.
12. $NR^{21}C(=O)NR^{12}R^{13}$.
13. $NR^{21}S(O)_2NR^{12}R^{13}$.
14. $PO(OR^{21})_2$.

Other additional aspects of the present invention include compounds of any of the preceding formulas wherein Ar, Y, $Z^1$, and $Z^2$, and q can be any moieties of the previous embodiments, and $R^1$ can be a combination of the values selected from the previous enumerated paragraphs. The preceding enumerated paragraphs may be combined to further define additional preferred embodiments of compounds of any of the preceding formulas. For example, one such combination includes $NR^{12}R^{13}$, $NR^{21}C(=O)R^{14}$, $C(=O)R^{15}$, COOH, $CO_2R^{14}$, $OC(=O)R^{11}$, $C(=O)NR^{12}R^{13}$, $C(=N)NR^{12}R^{13}$, $OC(=O)NR^{12}R^{13}$, $NR^{21}S(O)_2R^{11}$, $S(O)_2NR^{12}R^{13}$, $NR^{21}C(=O)NR^{12}R^{13}$, $NR^{21}S(O)_2NR^{12}R^{13}$, or $PO(OR^{21})_2$. An additional combination includes $NR^{12}R^{13}$, $NR^{21}C(=O)R^{14}$, $C(=O)NR^{12}R^{13}$, $C(=N)NR^{22}R^{13}$, $NR^{21}S(O)_2R^{11}$, $S(O)_2NR^{12}R^{13}NR^{21}S(O)NR^{12}R^{13}$, or $PO(OR^{21})_2$.

A third such combination includes $NR^{21}C(=O)R^{14}$, $C(=O)NR^{12}R^{13}$, $C(=N)NR^{12}R^{13}$, or $NR^{21}C(=O)NR^{12}R^{13}$.

Further aspects of the present invention include compounds of any of the preceding formulas wherein q, Ar, Y, and $R^1$ can be any moieties of the previous embodiments, and $R^{12}$ and $R^{13}$ is selected as follows. In one aspect, $R^{12}$ and $R^{13}$ are both H, or are both $C_1$-$C_6$ alkyl. In another aspect, one of $R^{12}$ and $R^{13}$ is H and the other is $C_1$-$C_6$ alkyl. In any of the above aspects, the $C_1$-$C_6$ alkyl groups are unsubstituted, or are substituted with one to three $R^{20}$ groups, or with one $R^{20}$ group, or with one to two CN, $OR^{21}$, $O(C_1$-$C_4$ alkylene)$OR^{21}$, $C(=O)NR^{23}R^{24}$, or 5-6 membered heteroaryl rings, particularly pyridyl. In other aspects, $R^{12}$ and $R^{13}$, together with the nitrogen to which they are attached, form a 3-7 membered heterocycloalkyl ring, particularly a 5-6 membered heterocycloalkyl ring, such as a pyrrolidinyl, piperidinyl, piperazinyl, or morpholinyl ring. In other aspects, they form a 5-6 membered heterocycloalkyl ring containing only one nitrogen, such as a pyrrolidinyl, or a piperidinyl ring. In any of the above aspects, said rings are unsubstituted, or are substituted with one to three $R^{20}$ groups, or with one $R^{20}$ group, or with an $OR^{21}$, $C(=O)R^{21}$, or $C(=O)NR^{23}R^{24}$ group.

The following terms and expressions contained herein are defined as follows:

As used herein, the term "about" refers to a range of values from +10% of a specified value. For example, the phrase "about 50 mg" includes ±10% of 50, or from 45 to 55 mg.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" refers to a straight chain, or branched hydrocarbon chains of 2 to 8 carbon atoms having at least one carbon-carbon triple bond. A designation "$C_2$-$C_8$ alkynyl" refers to an alkynyl radical containing from 2 to 8 carbon atoms. Examples include ethynyl, propynyl, isopropynyl, 3,5-hexadiynyl, etc.

As used herein, the term "alkylene" refers to a substituted or unsubstituted, branched or straight chained hydrocarbon of 1 to 8 carbon atoms, which is formed by the removal of two hydrogen atoms. A designation such as "$C_1$-$C_4$ alkylene" refers to an alkylene radical containing from 1 to 4 carbon atoms. Examples include methylene (—$CH_2$—), propylidene ($CH_3CH_2CH=$), 1,2-ethandiyl (—$CH_2CH_2$—), etc.

As used herein, the term "phenylene" refers to a phenyl group with an additional hydrogen atom removed, i.e. a moiety with the structure of:

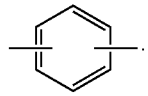

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_5$-$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include such groups as cyclopropyl, cyclobutyl, cyclopentyl, cyclohexl, cycloheptyl, cyclooctyl, pinenyl, and adamantanyl.

As used herein, the term "aryl" refers to a substituted or unsubstituted, mono- or bicyclic hydrocarbon aromatic ring system having 6 to 12 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the terms "heterocycle", "heterocyclic" or "heterocyclyl" refer to a substituted or unsubstituted carbocyclic group in which the ring portion includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

As used herein, the term "heterocycloalkyl" refers to a cycloalkyl group in which one or more ring carbon atoms are replaced by at least one hetero atom such as —O—, —N—, or —S—. Examples of heterocycloalkyl groups include pyrrolidinyl, pyrrolinyl, imidazolidinyl, imidazolinyl, pirazolidinyl, pirazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include pyrrolyl, furyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl, etc.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-NH$_2$. In certain embodiments, substituent groups for the compounds of the present invention include the residue of an amino acid after removal of the hydroxyl moiety of the carboxyl group thereof, i.e., groups of formula —C(=O)CH(NH$_2$)-(side chain). The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, 2$^{nd}$ ed.; Worth Publishers: New York, 1975; 71-77, the disclosure of which is incorporated herein by reference. Non-naturally occurring amino acids also include α-amino acids wherein the side chains are replaced with synthetic derivatives. Representative side chains of naturally occurring and non-naturally occurring α-amino acids are shown below in Table A.

TABLE A

| | | |
|---|---|---|
| H | CH$_3$ | CH(CH$_3$)$_2$ |
| CH$_2$CH(CH$_3$)$_2$ | CH(CH$_3$)CH$_2$CH$_3$ | CH$_2$OH |
| CH$_2$SH | CH(OH)CH$_3$ | CH$_2$CH$_2$SCH$_3$ |
| CH$_2$C$_6$H$_5$ | (CH$_2$)$_4$NH$_2$ | (CH$_2$)$_3$NHC(=NH)NH$_2$ |
| CH$_2$COOH | CH$_2$CH$_2$COOH | CH$_2$CONH$_2$ |
| CH$_2$CH$_2$CONH$_2$ | CH$_2$CH$_3$ | CH$_2$CH$_2$CH$_3$ |
| CH$_2$CH$_2$CH$_2$CH$_3$ | CH$_2$CH$_2$SH | CH$_2$CH$_2$OH |
| CH$_2$CH$_2$SCH$_3$ | (CH$_2$)$_3$NH$_2$ | (CH$_2$)$_2$CH(OH)CH$_2$NH$_2$ |
| (CH$_2$)$_3$NHC(=O)NH$_2$ | (CH$_2$)$_2$ONHC(=NH)NH$_2$ | CH$_2$C(=O)NHCH$_2$COOH |

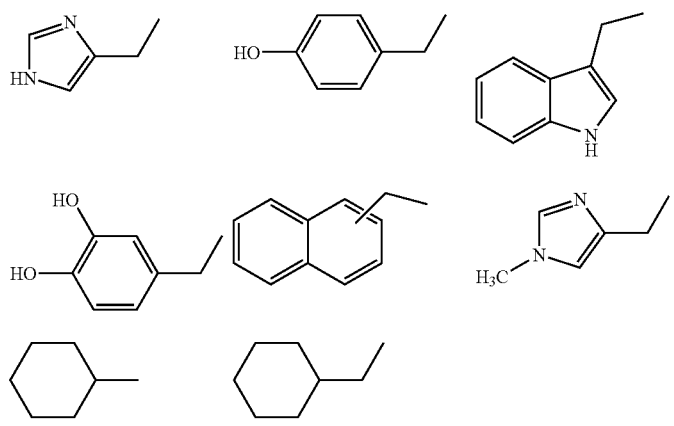

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety It is recognized that compounds of the present invention may exist in various stereoisomeric forms. As such, the compounds of the present invention include all stereoisomeric forms, such as the diastereomeric and enantiomeric forms. The compounds are normally prepared as racemates and can conveniently be used as such, but individual stereoisomers can be isolated or synthesized by conventional techniques if so desired. Such stereoisomeric forms are included in the present invention, including the racemates, individual enantiomers and diastereomers, and mixtures thereof.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of the present invention may contain protecting groups. For example, the amino acid side chain substituents of the compounds of the present invention can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P.G.M., "Protective Groups in Organic Synthesis" 2d. Ed., Wiley & Sons, 1991.

SYNTHESIS AND EXAMPLES

The compounds of the present invention may be prepared in a number of methods well known to those skilled in the art, including, but not limited to those described below, or through modifications of these methods by applying standard techniques known to those skilled in the art of organic synthesis. The reagents and starting materials are commercially available, or readily synthesized by well-known techniques by one of ordinary skill in the arts. All substituents in the synthetic schemes, unless otherwise indicated, are as previously defined. All processes disclosed in association with the present invention are contemplated to be practiced on any scale, including milligram, gram, multigram, kilogram, multikilogram or commercial industrial scale.

Illustrative of compounds encompassed by the present invention that are useful in the utilities disclosed herein include those set forth in the following tables. This list is meant to be representative only and is not intended to limit the scope of the invention in any way.

Scheme A: General Scheme

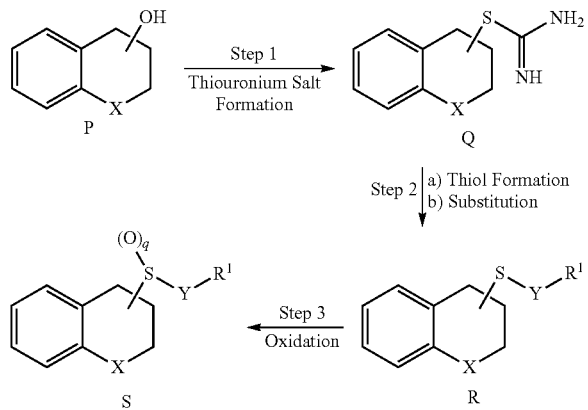

Step 1: Synthesis of Compounds of General Structure Q:

In step 1, the alcohol moiety of compound P is converted to the corresponding thiouronium salt. For example, an appropriate amount of thiourea is taken into 48% HBr and water. The mixture is warmed (preferably to 60-70° C.), followed by addition of compound P. The temperature of the reaction mixture is elevated (preferably to 90-95° C.) and the stirring is continued for an additional period of time for completion of the reaction. The reaction mixture is cooled to room temperature (in some cases, an ice-bath might be needed) and the precipitated solid is filtered and thoroughly washed with water to generate compound Q.

Step 2: Synthesis of Compounds of General Structure R:

In step 2a, the thiouronium salt Q from previous step is converted to corresponding thiol. In step 2b, the thiol undergoes a substitution reaction with an appropriate reactant to generate compound R. Thus, compound Q from step 1 is taken into additional water and treated with an aqueous base, preferably a sodium hydroxide solution. The mixture is warmed (preferably to 70-80° C., but in some cases a higher temperature might be needed) and to it an appropriate amount of a reactant of generic structure W—Y—$R^1$ (where W is a suitable leaving group) in water (or in some cases, an alcoholic solvent) is added. The reaction mixture is maintained at an elevated temperature (preferably 100-110° C.) for an appropriate period of time, cooled, taken into water and washed with an organic solvent (preferably ether). The basic aqueous layer is acidified with an inorganic acid solution (e.g. aqueous HCl solution). The aqueous (acidic) solution is then extracted several times into an organic solvent (e.g. ether or ethyl acetate). The combined organic layer is washed with brine, dried ($MgSO_4$ or $Na_2SO_4$) and concentrated to give the crude product that may be used directly in the next step. However, purification could be achieved by employing known purification techniques (e.g. recrystallization) to provide pure compound R. The method is an adaptation from a procedure previously described in U.S. Pat. No. 4,177,290, incorporated by reference herein in its entirety.

Step 3: Synthesis of Compounds of General Structure S:

Compounds of structure R may optionally be oxidized to generate compounds of structure S. Thus, compound S is prepared by reacting compound R in an appropriate solvent with an appropriate oxidizing agent. An appropriate oxidizing agent is one that oxidizes the sulfide group of compound R. The corresponding product is isolated and purified by methods well known in the art. For example, to a cooled (−15° C. to −25° C.) solution of compound R in an organic solvent (preferably methylene chloride or chloroform), an appropriate oxidizing agent (e.g. m-chloroperoxybenzoic acid ["m-CPBA"], 1 equivalent) in the same solvent is slowly added. Stirring is continued at low temperature until the disappearance of the starting material, as evidenced by various analytical techniques. The reaction mixture is then thoroughly washed with a saturated sodium bicarbonate solution, water and brine, respectively, dried over a drying agent (e.g. $MgSO_4$ or $Na_2SO_4$) and concentrated. The desired product (compound S) is purified, if needed, by employing known purification techniques (preferably by column chromatography and/or recrystallization). In other cases, the oxidation is performed by employing 50% $H_2O_2$ in glacial acetic acid solvent.

Scheme B: 1-Indanes

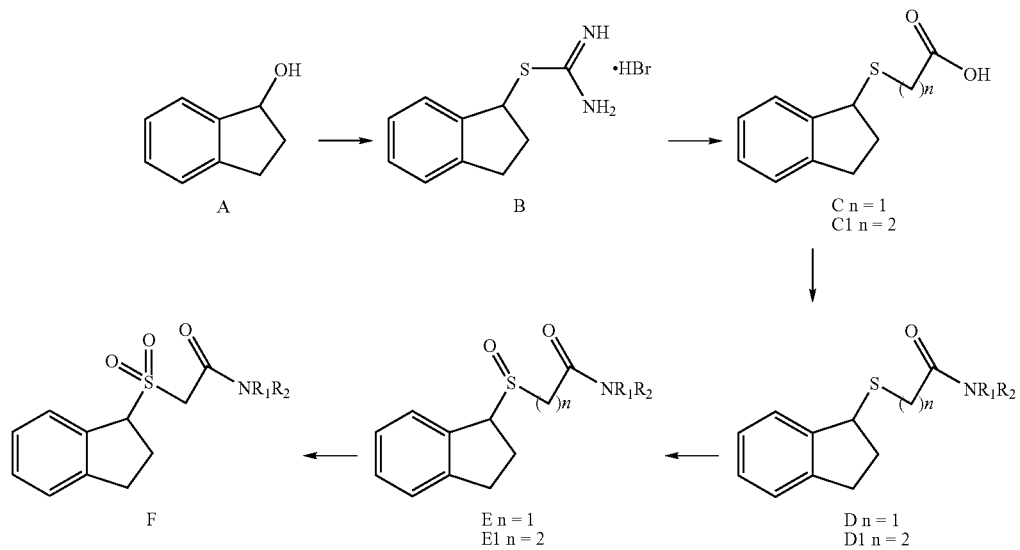

Example 1

Synthesis of Compound C

To a mixture of thiourea (8.3 g, 109 mmol) and 48% HBr (76 mL, 705 mmol) at 60° C. was added compound A (10 g, 75 mmole) in portions. The reaction mixture was then gently heated to reflux for 1 h, cooled and filtered. The residue was washed successively with water and ether, and dried in vacuo to yield compound 10.7 g of compound B (white solid) that was directly used in the next step without any further purification. Thus, to a mixture of compound B (6 g, 22 mmol) and aq. NaOH (12.5%, 17.6 mL) at 70° C. was added slowly a solution of chloroacetic acid (2.3 g, 24 mmol) in aq. NaOH (3.3%, 2.3 mL). The reaction mixture was then heated at 110° C. for 1 h, cooled, diluted with ice-water, washed with ether and acidified (pH ~2). The resultant acidic mixture was extracted into ethyl acetate (3×100 mL). The combined organic layer was washed with brine (1×100 mL), dried over $MgSO_4$, and concentrated to yield compound C (3 g, semi-solid, $R_t$: 9.90 min). This compound was directly used in the next step without any further purification.

Example 2

Synthesis of Compound C1

This compound was prepared following the same procedure as described in Example 2 using 2-bromopropionic acid in place of chloroacetic acid; $R_t$: 10.81 min.

Example 3

Synthesis of Compound D ($NR_1R_2$=$NH_2$)

To a cooled (ice-bath) mixture of compound C (3 g, 14 mmol), and EDCI (3.3 g, 17 mmol) in DMF (15 mL) was added $NH_3$.HOBt-complex (2.7 g, 18 mmol). The cooling bath was removed and the mixture was stirred at room temperature for 1 h. It was then diluted with ethyl acetate (100 mL), washed successively with water (1×50 mL), 2% aq. citric acid (2×50 mL), water (1×50 mL), 2% aq. $NaHCO_3$ (2×50 mL), water (1×50 mL), and brine (1×50 mL) and dried ($MgSO_4$). On concentration, the solution generated a solid product that was filtered, washed with ether and dried to give 1.76 g of compound D ($NR^1R_2$=$NH_2$); $R_t$: 8.58 min.

Example 4

Synthesis of Compound D1 ($NR_1R_2$=$NH_2$)

This compound was prepared following the same procedure as described in Example 3 using C1 in place of C.

Example 5

Synthesis of Compound D ($NR_1R_2$=N-pyrrolidinyl)

To a cooled (ice-bath) mixture of compound C (1.5 g, 7.2 mmol), and 2-(1H-benzotriazol-1-yl)-1,1,3,3-tetramethyluronium tetrafluoroborate (TBTU, 3.5 g, 11 mmol), and pyrrolidine (720 μL, 8.6 mmol) in DMF (15 mL) was added NMM (N-methylmorpholine, 1.2 mL, 11 mmol). The cooling bath was removed and the mixture was stirred at room temperature for 1 h. It was then diluted with ethyl acetate (100 mL), washed successively with water (1×50 mL), 2% aq. citric acid (2×50 mL), water (1×50 mL), 2% aq. $NaHCO_3$ (2×50 mL), water (1×50 mL), and brine (1×50 mL) and dried ($MgSO_4$). Solvent evaporation gave a crude product that was purified by flash chromatography (ethyl acetate) to give 1.11 g of compound D ($NR_1R_2$=N-pyrrolidinyl); $R_t$: 11.13 min.

Examples 6-8

Synthesis of Compounds D ($NR_1R_2$=N-pyrrolidinyl-2-(S)-carboxamide, $NMe_2$, N-(4-acetyl)-piperazinyl, respectively)

These compounds were prepared from compound C following the same procedure as described in Example 5 using the appropriate amine.

Example 9

Synthesis of Compound D1 ($NR_1R_2$=N-(4-acetyl)-piperazinyl))

This compound was prepared following the same procedure as described in Example 5 using the appropriate amine.

Example 10

Synthesis of Compound E ($NR_1R_2$=$NH_2$)

To a cooled solution (ice-bath) of compound D ($NR_1R_2$=$NH_2$, 1.76 g, 8.5 mmol) in glacial acetic acid (8 ml) was added 50% aqueous $H_2O_2$ (1.3 eqv). The ice-bath was removed and the mixture was stirred until no more starting material was detected (HPLC), concentrated at high vacuum and triturated with ether to give a solid that was dried on a lyophilizer to generate 1.69 g of compound E ($NR_1R_2$=$NH_2$).

Analytical data: $^1$H-NMR (DMSO-$d_6$) δ 7.69 (d, 1H), 7.46-7.18 (m, 5H), 4.43-3.66 (m, 1H), 3.65-3.44 (m, 2H), 3.04-2.86 (m, 2H), 2.60-2.19 (m, 2H).

Example 11

Synthesis of Compound E1 ($NR_1R_2$=$NH_2$)

This compound was prepared from compound D1 following the same procedure as described in Example 10 using compound C1 and the appropriate amine.

Analytical Data: $^1$H-NMR (DMSO-$d_6$) δ 7.50 (s, 1H), 7.45 (m, 1H), 7.25 (m, 3H), 6.95 (s, 1H), 4.40 (m, 1H), 2.95 (m, 3H), 2.90 (m, 1H), 2.50-2.10 (m, 4H).

Example 12

Synthesis of Compound E ($NR_1R_2$=N-pyrrolidinyl)

This compound was prepared, following the same procedure as described in Example 10 using compound C and the appropriate amine.

Analytical data: $^1$H-NMR (DMSO-$d_6$) δ 7.43 (t, 1H), 7.34-7.18 (m, 3H), 4.55 (q, 1H), 3.88-3.75 (m, 2H), 3.56-3.27 (m, 4H), 3.03-2.86 (m, 2H), 2.64-2.53 (m, 1H), 2.47-2.17 (m, 1H), 1.91-1.74 (m, 4H).

Example 13

Synthesis of Compound E ($NR_1R_2$=N-pyrrolidinyl-2-(S)-carboxamide)

This compound was prepared, following the same procedure as described in Example 10 using compound C and the appropriate amine.

Example 14

Synthesis of Compound E (NR$_1$R$_2$=NMe$_2$)

This compound was prepared, following the same procedure as described in Example 10 using compound C and the appropriate amine.

Analytical data: $^1$H-NMR (DMSO-d$_6$) δ 7.41 (t, 1H), 7.34-7.18 (m, 3H), 4.55-4.49 (m, 1H), 3.89 (q, 2H), 3.03 (s, 3H), 3.01-2.89 (m, 2H), 2.86 (s, 3H), 2.64-2.17 (m, 2H).

Example 15

Synthesis of Compound E (NR$_1$R$_2$=N-(4-acetyl)-piperazinyl)

This compound was prepared, following the same procedure as described in Example 10 using compound C and the appropriate amine.

Analytical data: $^1$H-NMR (DMSO-d$_6$) δ 7.44 (t, 1H), 7.34-7.19 (m, 3H), 4.25 (d, 1H), 4.03-3.92 (m, 2H), 3.61-3.32 (m, 8H), 3.06-2.87 (m, 2H), 2.66-2.17 (m, 2H), 2.06-1.99 (s, 3H).

Example 16

Synthesis of Compound E1 (NR$_1$R$_2$=N-(4-acetyl)-piperazinyl)

This compound was prepared following the same procedure as described in Example 10 using compound C1 and the appropriate amine.

Analytical Data: $^1$H-NMR (DMSO-d$_6$) δ 7.45 (m, 1H), 7.30 (m, 3H), 4.45 (m, 1H), 3.50 (m, 8H), 3.00 (m, 3H), 3.80 (m, 3H), 2.30 (m, 2H), 2.00 (s, 3H).

Example 17

Synthesis of Compound F (NR$_1$R$_2$=NH$_2$)

A mixture of compound E (NR$_1$R$_2$=NH$_2$, 0.3 g, 1.46 mmol) and m-chloroperbenzoic acid (77%, 0.5 g, 2.92 mmol) in methylene chloride (10 mL) was stirred at room temperature for 0.5 h. The reaction mixture was diluted with methylene chloride (20 mL) and washed with 2% NaHCO$_3$ (3×25 mL), water (1×20 mL), and brine (1×25 mL), dried (MgSO$_4$), concentrated and triturated with cold ether to generate 0.14 g of compound F.

Analytical data: $^1$H-NMR (DMSO-d$_6$): δ 7.80 (s, 1H), 7.50 (d, 2H), 7.30 (d, 2H), 7.25 (m, 1H), 5.00 (m, 1H), 4.15 (d, 1H), 4.00 (d, 1H), 3.05 (m, 1H), 2.90 (m, 1H), 2.60 (m, 1H), 2.50 (m, 1H).

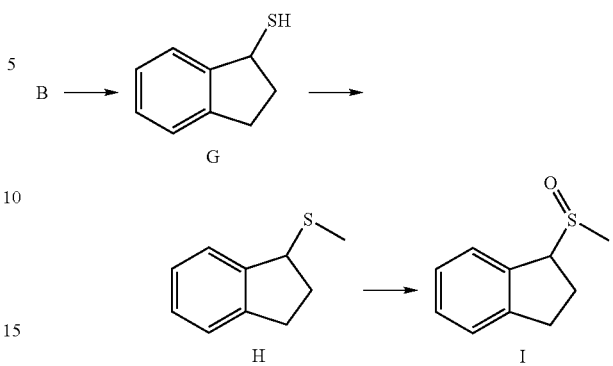

Scheme C

Example 18

Synthesis of Compound H

A mixture of compound B (4 g, 15 mmol) and 10 N NaOH (6 ml), and water (37 mL) was heated at 70° C. for 0.5 h, cooled, diluted with ice-water and acidified (pH ~2). The acidic solution was extracted with ethyl acetate (3×100 mL). The combined organic layers were washed with brine (1×50 mL), dried (MgSO$_4$), and concentrated to yield 1.59 g of compound G (white solid; R$_t$: 13.67 min) that was directly used in the next step. Thus, a mixture of compound G (1.58 g, 10.5 mmol) in methanol (14 mL) and sodium methoxide in methanol (0.5 M, 21 mL) was heated at 60° C. for 0.5 h, cooled and treated with iodomethane (2 mL, 32 mmol). The reaction was stirred at 60° C. for 7 h, cooled, diluted with ice-water and acidified (pH 2). The acidic solution was extracted with ethyl acetate (3×100 mL). The combined organic layers were washed with brine (1×50 mL), dried (MgSO$_4$), and concentrated to yield compound H (1.3 g, R$_t$: 14.12 min) that was directly used in the next step without any further purification.

Example 19

Synthesis of Compound I

Starting with compound H, this compound was prepared following the same procedure as described in Example 10.

Analytical data: $^1$H-NMR (CHCl3-d) δ 7.44 (q, 1H), 7.32-7.20 (m, 3H), 4.34 (dq, 1H), 3.15-2.94 (m, 2H), 2.64-2.39 (m, 2H), 2.35 (s, 3H).

Scheme D: Chromans

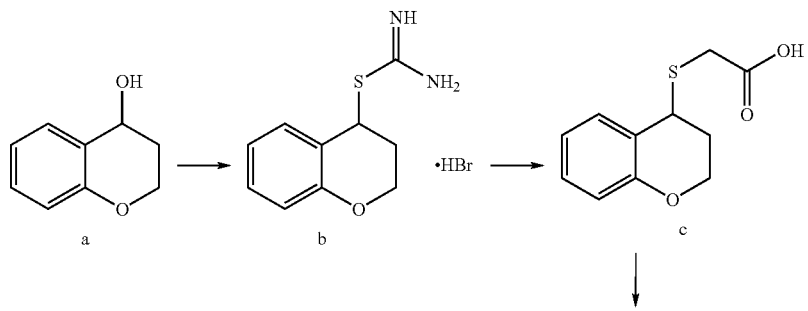

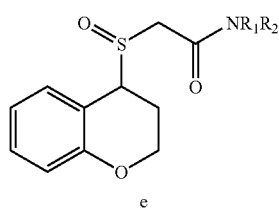

e

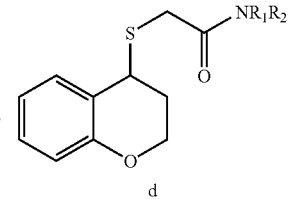

d

Example 20

Synthesis of Compound c

To a mixture of thiourea (2.84 g, 37.3 mmol) and 48% HBr (10 mL, 80 mmol) in water (50 mL) at 60° C. was added compound a (4 g, 26.6 mmol) in portions. The reaction mixture was then gently heated to reflux for 1 h, cooled and filtered. The residue was washed successively with water and ether, triturated with ethyl acetate and dried in vacuo to yield compound b (10.7 g, white solid) that was directly used in the next step without any further purification. Thus, to a mixture of compound b (4.08 g, 14.1 mmol), aq. NaOH (10 N, 5.6 mL), and water (35 mL) at 70° C. was added, slowly a solution of chloroacetic acid (1.87 g, 19.7 mmol) in water (6 mL). The reaction mixture was then stirred at 100° C. for 2.5 h, cooled, diluted with ice-water, washed with ether and acidified (pH ~2). The resultant acidic mixture was extracted into ethyl acetate (3×100 mL). The combined organic layer was washed with brine (1×100 mL), dried (MgSO$_4$), and concentrated to yield compound c (2.27 g, viscous oil). This compound was directly used in the next step without any further purification.

Example 21

Synthesis of Compound d (NR$_1$R$_2$=NH$_2$)

To a cooled (ice-bath) mixture of compound c (2.14 g, 7.45 mmol), NMM (1.47 mL, 13.3 mmol) and TBTU (3.37 g, 10.5 mmol) in DMF (30 mL) was added NH$_3$.HOBt-complex (2.9 g, 19 mmol). The cooling bath was removed and the mixture was stirred at room temperature for 4 h. It was then diluted with ethyl acetate (100 mL), washed successively with water (1×50 mL), 2% aq. citric acid (2×50 mL), water (1×50 mL), 2% aq. NaHCO$_3$ (2×50 mL), water (1×50 mL), and brine (1×50 mL) and dried (MgSO$_4$). On concentration, the solution generated a solid product that was filtered, triturated with ether and dried to give 0.84 g of compound d (NR$_1$R$_2$=NH$_2$).

Examples 22-24

Synthesis of Compound d (NR$_1$R$_2$=N-pyrrolidinyl, NHCH$_2$-(3-pyridyl), NHCH$_2$CHMe$_2$, Respectively)

These compounds were prepared from compound c, following the same procedure as described in Example 21 using the appropriate amine.

Example 25

Synthesis of Compound d (NR$_1$R$_2$=NMe$_2$)

To a refluxing solution of compound c (1.81 g, 8.1 mol) in benzene (20 mL) was added thionyl chloride (3.18 mL) dropwise. The reaction mixture was refluxed for an additional 1 h, and concentrated to remove the volatiles to generate the corresponding acid-chloride. This material was re-dissolved in methylene chloride (25 mL) and treated with dimethylamine gas. It was then stirred for 6 h at room temperature, washed successively with water (2×20 mL), sat. NaHCO$_3$ solution (2×25 mL), water (1×25 mL), and brine (1×25 mL), dried (Na$_2$SO$_4$) and concentrated to generate 2.14 g of compound d (NR$_1$R$_2$=NMe$_2$) that was directly used in next step.

Example 26

Synthesis of Compound e (NR$_1$R$_2$=NH$_2$)

This compound was synthesized by oxidation of corresponding compound d as described in Example 10.
Analytical data: $^1$H-NMR (DMSO-d$_6$) δ 7.73 (s, 1H), 7.36 (d, 1H), 7.22 (m, 2H), 6.93 (dt, 1H), 6.84 (d, 1H), 4.27-4.12 (m, 3H), 3.72 (q, 1H), 3.69 (dd, 1H), 2.55-2.15 (m, 2H).

Example 27

Synthesis of Compound e (NR$_1$R$_2$=N-pyrrolidinyl)

This compound was synthesized by oxidation of corresponding compound d as described in Example 10.
Analytical data: $^1$H-NMR (DMSO-d$_6$) δ 7.43-6.83 (m, 4H), 4.33-3.87 (m, 5H), 3.58-3.44 (m, 2H), 3.41-3.33 (m, 1H), 2.59-2.16 (m, 3H), 1.92-1.76 (m, 4H).

Example 28

Synthesis of Compound e (NR$_2$=NMe$_2$)

This compound was synthesized by oxidation of corresponding compound d as described in Example 10.
Analytical data: $^1$H-NMR (DMSO-d$_6$) δ.7.43-6.82 (m, 4H), 4.30-3.98 (m, 5H), 3.04 (s, 3H), 2.87 (s, 3H), 2.70-2.52 (m, 1H), 2.36-2.16 (m, 2H).

Example 29

Synthesis of Compound e (NR$_1$R$_2$=NHCH$_2$-(3-pyridyl))

This compound was synthesized by oxidation of corresponding compound d as described in Example 10.
Analytical data: $^1$H-NMR (DMSO-d$_6$): δ11.90 (bs, 1H), 8.90 (s, 1H), 8.50-8.45 (m, 2H), 7.75 (d, 1H), 7.30 (t, 1H), 7.25 (m, 1H), 6.80-7.00 (m, 2H), 4.40-4.01 (m, 6H), 4.00-3.70 (m, 2H), 2.40-2.20 (m, 2H), 1.90 (s, 3H).

Example 30

Synthesis of Compound e (NR$_1$R$_2$=NHCH$_2$CHMe$_2$)

This compound was synthesized by oxidation of corresponding compound d as described in Example 10.
Analytical data: $^1$H-NMR (DMSO-d$_6$): δ 8.20 (t, 2H), 7.35-7.20 (m, 2H), 7.00-6.80 (m, 3H), 4.30-4.10 (m, 6H), 3.90-3.50 (m, 5H), 2.40-2.10 (m, 3H).

Scheme E: Thiochromans

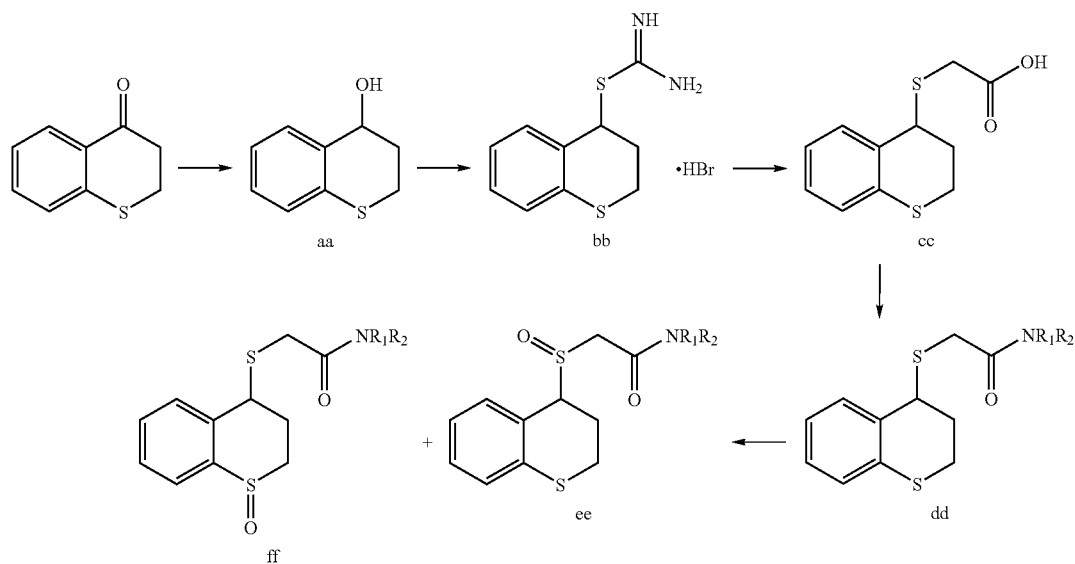

Example 31

Synthesis of Compound cc

To a solution of thiochroman-4-one (9.95 g, 60.6 mmol) in anhydrous ethanol (73 mL) was added sodium borohydride (2.29 g) in small portions. The reaction mixture was stirred at room temperature for 1 h, evaporated to dryness, and treated with ice-water. The aqueous layer was acidified (pH ~2), and extracted into ethyl acetate (3×100 mL). The combined organic layers were washed with water (1×50 ml) and brine (1×50 mL), dried (MgSO$_4$), and concentrated to give 9.32 g of compound aa; $^1$H-NMR (DMSO-d$_6$) δ 7.35-6.83 (m, 4H), 5.32 (br s, 1H), 4.59 (m, 1H), 3.32-3.13 (m, 1H), 2.95-2.89 (m, 1H), 2.12-2.05 (m, 1H), 1.99-1.92 (m, 1H).

Compound aa was converted to compound cc via compound bb following the same procedure in Example 20.

Example 32

Synthesis of Compound dd (NR$_1$R$_2$=NMe$_2$)

This compound was prepared from compound cc, following the same procedure as described in Example 25.

Analytical data: $^1$H-NMR (DMSO-d$_6$) δ 7.27-6.98 (m, 4H), 4.35 (m, 1H), 3.54-3.38 (m, 3H), 3.02 (s, 3H), 2.99-2.91 (m, 1H), 2.86 (s, 3H), 2.50-2.44 (m, 1H), 2.07-1.99 (m, 1H).

Examples 33-34

Synthesis of Compound ee (NR$_1$R$_2$=NMe$_2$) and compound ff (NR$_1$R$_2$=NMe$_2$), respectively To a solution of compound dd (NR$_1$R$_2$=NMe$_2$)(3.39 g, 12.8 mmol) in glacial acetic acid (40 mL) at room temperature was added aq. H$_2$O$_2$ (50%, 812 μL, 14 mmol). The mixture was stirred for 5.5 h, diluted with water, and extracted into ethyl acetate (3×50 mL). The combined organic layers were washed with 2% aq. NaHCO$_3$ (2×50 mL). The basic wash layer was re-extracted into ethyl acetate (2×50 mL). Combined organic layer was washed with water (1×50 mL), brine (1×50 mL), dried (MgSO$_4$), and concentrated to give a residue that was purified by silica-gel flash chromatography (9:1:: ethyl acetate—methanol) to provide 0.168 mg of compound ee (NR$_1$R$_2$=NMe$_2$)(less polar, eluted first) and 0.291 mg of compound ff (NR$_1$R$_2$=NMe$_2$)(more polar, eluted later), respectively.

Analytical Data: Compound ee (NR$_1$R$_2$=NMe$_2$): $^1$H-NMR (DMSO-d$_6$) δ 7.45 (d, 1H), 7.22-7.06 (m, 3H), 4.45 (t, 1H), 4.0.1 (q, 1H), 3.38-3.32 (m, 1H), 3.02 (s, 3H), 3.00-2.97 (m, 1H), 2.85 (s, 3H), 2.84-2.79 (m, 1H), 2.22-2.08 (m, 1H).

Compound ff (NR$_1$R$_2$=NMe$_2$): $^1$H-NMR (DMSO-d$_6$) δ 7.69-7.45 (m, 4H), 4.54 (t, 1H), 3.61-3.53 (m, 2H), 3.50-3.43 (m, 1H), 3.06-3.04 (m, 1H), 3.01 (s, 3H), 2.85 (s, 3H), 2.72-2.63 (m, 1H), 2.29-2.23 (m, 1H).

Scheme F: Naphthalenes

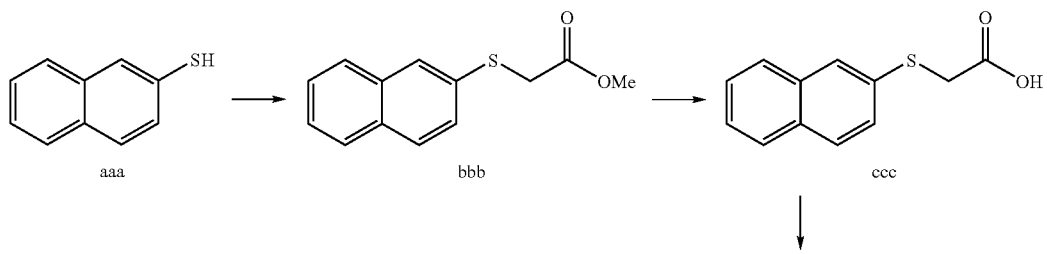

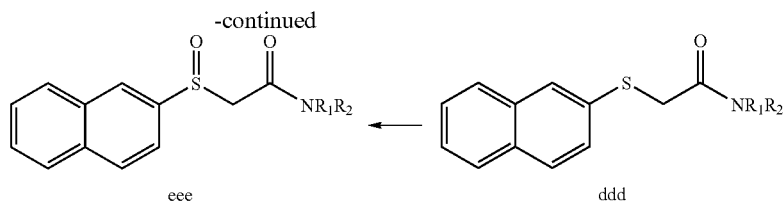

Examples 35-36

Synthesis of Compounds bbb and ee, Respectively

To a stirred slurry of NaH in oil (60%, 3 g, 0.075 mol) in anhydrous THF (50 mL) at 0° C., was slowly added compound aaa (11.3 g, 0.070 mol) in anhydrous THF (50 ml). After the evolution of hydrogen gas ceased, a solution of methyl bromoacetate (11.4 g, 0.075 mol) in anhydrous THF (40 mL) was added dropwise to the reaction mixture. Stirring was continued for another 1 h at room temperature. The reaction mixture was then quenched with ice-water (100 mL) and extracted into diethyl ether (3×200 ml). The combined organic layers were washed with water (1×50 mL) and brine (1×50 mL), dried ($MgSO_4$), and concentrated to generate a crude product that was triturated with petroleum ether followed by diethyl ether to obtain 14.2 g of compound bbb (off-white solid) that was directly used in the next step. Thus, a mixture of compound bbb (11.1 g), methanol (70 mL), and aq. NaOH (1.2 N, 60 ml) was stirred at room temperature for several hours, diluted with water (80 mL), cooled (ice-bath) and acidified (pH ~2). The precipitate was filtered, washed with cold water and dried under high vacuum to generate compound ccc (8.7 g, white solid) that was directly used in the next step without further purification.

Examples 37-43

Synthesis of Compound ddd ($NR_1R_2$=$NH_2$, NH—(S)—$CH(CH_3)CONH_2$, $NH(CH_2)_2OH$, N-pyrrolidinyl, NH—(S)—$CH(CH_2CONH_2)CONH_2$, N-pyrrolidinyl-2-(S)-carboxamide, $NMe_2$, respectively)

These compounds were prepared from compound ccc following the same procedure as described in Example 3 using the appropriate amine.

Example 44

Synthesis of Compound eee ($NR_1R_2$=$NH_2$)

This compound was prepared from compound ddd following the same procedure as described in Example 10.

Analytical data: $^1$H-NMR (DMSO-$d_6$) δ 8.32 (s, 1H), 8.15-8.05 (m, 3H), 7.62 (d, 1H), 7.55 (m, 2H), 7.5 (s, 1H), 7.25 (s, 1H), 3.85 (q, 2H).

Example 45

Synthesis of Compound eee ($NR_1R_2$=NH—(S)—$CH(CH_3)CONH_2$)

This compound was prepared from compound ddd following the same procedure as described in Example 10.

Analytical data: $^1$H-NMR (DMSO-$d_6$) δ 8.25 (d, 1H), 7.86 (m, 4H), 7.5 (m, 3H), 7.45 (s, 1H), 7.0 (s, 1H), 4.21 (m, 1H), 3.95 (q, 2H), 1.25 (d, 3H).

Example 46

Synthesis of Compound eee ($NR_1R_2$=$NH(CH_2)_2OH$)

This compound was prepared from compound ddd following the same procedure as described in Example 10.

Analytical Data: $^1$H-NMR (DMSO-$d_6$) δ 8.32 (s, 1H), 8.25-8.00 (m, 4H), 7.81 (d, 2H), 7.7 (m, 1H), 4.82 (t, 1H), 3.95 (q, 2H), 3.26 (m, 2H), 3.15 (m, 2H).

Example 47

Synthesis of Compound eee ($NR_1R_2$=N-pyrrolidinyl)

This compound was prepared from compound ddd following the same procedure as described before for the synthesis of compound E ($NR_1R_2$=$NH_2$) from compound D.

Analytical Data: $^1$H-NMR (DMSO-$d_6$) δ 8.32 (s, 1H), 8.25-8.00 (m, 4H), 7.81 (d, 1H), 7.70 (m, 2H), 4.01 (s, 2H), 3.55 (m, 1H), 3.26 (m, 2H), 1.74 (m, 4H).

Example 48

Synthesis of Compound eee ($NR_1R_2$=NH—(S)—$CH(CH_2CONH_2)CONH_2$)

This compound was prepared from compound ddd following the same procedure as described in Example 10.

Analytical Data: $^1$H-NMR (DMSO-$d_6$) δ 8.50 (q, 1H), 8.25 (d, 1H), 8.00 (m, 3H), 7.80 (m, 1H), 7.65 (m, 2H), 7.40-6.91 (m, 4H), 4.50 (m, 1H), 3.95 (m, 2H), 2.45 (m, 2H).

Example 49

Synthesis of Compound eee ($NR_1R_2$=N-pyrrolidinyl-2-(S)-carboxamide)

This compound was prepared from compound ddd, following the same procedure as described in Example 10.

Analytical Data: $^1$H-NMR (DMSO-$d_6$) δ 8.45-6.95 (m, 9H), 4.45-4.25 (dd, 1H), 4.10 (m, 2H), 3.50 (m, 2H), 2.20-1.80 (m, 4H).

Example 50

Synthesis of Compound eee ($NR_1R_2$=$NMe_2$)

This compound was prepared from compound ddd following the same procedure as described in Example 10.

Scheme G: 2-Indanes aaaa R = OH
bbbb R = Br cccc n = 1
cccc1 n = 2 ffff dddd n = 1
dddd1 n = 2 gggg eeee n = 1
eeee1 n = 2

Preparation 1

Synthesis of Compound bbbb

To a stirred solution of compound aaaa (26.8 g, 200 mmol) and triphenylphosphine (55.2 g, 210 mmol) in dry $CH_2Cl_2$ (400 ml) under $N_2$ was slowly added bromine (10.8 mL, 212 mmol) at 0° C. The cooling bath was removed and the reaction was stirred at room temperature for an additional 2 h. It was then concentrated under reduced pressure with gentle heating (40° C.) and the hot residue was slowly poured into $Et_2O$ (400 ml) with vigorous stirring. The solution was cooled at 0° C. for 15 min and filtered. The filtrate was washed with 5% aq. $Na_2SO_3$ solution, water, dried ($MgSO_4$) and evaporated to give compound bbbb (38.4 g, $R_f$=0.75 in 9:1 cyclohexane/ethyl acetate) as an oil that was directly used in the subsequent step without any further purification. The method was an adaptation from a procedure previously described in *J Med. Chem.* 1994, 37, 1586-1601, incorporated herein by reference in its entirety.

Example 51

Synthesis of Compound cccc

To a cooled (ice-bath) solution of potassium t-butylate (6.9 g, 61 mmol) in dry methanol (150 ml) under $N_2$ was added methyl 2-sulfanyl acetate (5.5 mL, 62 mmol). The reaction mixture was stirred for an additional 10 min and to it a solution of compound bbbb (10 g, 51 mmol) in dry methanol (20 ml) was slowly added. The ice-bath was removed and the reaction mixture was refluxed for 1 h., concentrated to dryness and quenched with sat. ammonium chloride solution (200 ml). It was then extracted into ethyl acetate (2×150 ml). The combined organic layers were dried ($MgSO_4$), concentrated in vacuo to generate a crude product that was purified by silica gel column chromatography (cyclohexane:ethyl acetate::9:1) to afford 8.46 g of compound cccc (oil, $R_f$=0.32 in 9:1 cyclohexane/ethyl acetate).

Example 52

Synthesis of Compound cccc1

This compound was prepared from compound bbbb following the same procedure as described in Example 51 using methyl 3-sulfanylpropanoate in place of methyl 2-sulfanyl acetate. $R_f$=0.36 (9:1 cyclohexane/ethyl acetate).

Example 53

Synthesis of Compound dddd ($NR_1R_2$=N-pyrrolidinyl)

To a solution of compound cccc (1 g, 4.5 mmol) in dichloromethane (20 mL) at room temperature was added pyrrolidine (0.45 mL, 5.4 mmol) followed by a solution of trimethylaluminium hydride in toluene (2M, 2.7 mL, 5.4 mmol). The reaction mixture was stirred for 96 h, diluted with dichloromethane (50 mL) and carefully quenched with 1N HCl solution (dropwise; 50 mL). The organic layer was separated and concentrated to give a crude product that was purified by silica gel column chromatography (dichloromethane:methanol:: 98:2) to generate 0.78 g of compound dddd ($NR_1R_2$=N-pyrrolidinyl). $R_f$=0.24 (98:2 dichloromethane/methanol).

Example 54

Synthesis of Compound dddd1 ($NR_1R_2$=$NH_2$)

A mixture of compound cccc1 (1 g; 4.2 mmol), MeOH (40 mL) and 28% $NH_4OH$ (40 mL) was stirred at room temperature overnight, concentrated to dryness, triturated with water and filtered. The residue was washed several times with water and dried in vacuo to generate 0.64 g of compound dddd1 ($NR_1R_2$=$NH_2$) that was directly used in the next step without any further purification.
Analytical Data: $^1$H-NMR (DMSO-$d_6$) δ: 7.35 (s, 1H), 7.2 (m, 2H), 7.1 (m, 2H), 6.85 (s, 1H), 3.65 (m, 1H), 3.35-3.25 (m, 2H), 2.85-2.7 (m, 4H), 2.35 (t, 2H).

Example 55

Synthesis of Compound dddd ($NR_1R_2$=$NH_2$)

This compound was prepared from compound cccc following the same procedure as described in Example 54.
$R_f$=0.41 (95:5 dichloromethane/methanol).

Example 56

Synthesis of Compound dddd ($NR_1R_2$=$NMe_2$)

This compound was prepared from compound cccc following the same procedure as described in Example 53 using the appropriate amine.
$R_f$=0.27 (98:2 dichloromethane/methanol).

Example 57

Synthesis of Compound dddd ($NR_1R_2$=$NHCHMe_2$)

This compound was prepared from compound cccc following the same procedure as described in Example 53 using the appropriate amine.
$R_f$=0.35 (98:2 dichloromethane/methanol).

Example 58

Synthesis of Compound dddd (NR$_1$R$_2$=N-(4-acetyl)-piperazinyl))

This compound was prepared from compound cccc following the same procedure as described in Example 53 using the appropriate amine.
R$_f$=0.33 (94:6 dichloromethane/methanol).

Example 59

Synthesis of Compound dddd1 (NR$_1$R$_2$=N-pyrrolidinyl)

This compound was prepared from compound cccc1 following the same procedure as described in Example 53 using the appropriate amine.
R$_f$=0.27 (98:2 dichloromethane/methanol).

Example 60

Synthesis of Compound dddd1 (NR$_1$R$_2$=NHCHMe$_2$)

This compound was prepared from compound cccc1 following the same procedure as described in Example 53 using the appropriate amine.
R$_f$=0.25 (98:2 dichloromethane/methanol).

Example 61

Synthesis of Compound dddd1 (NR$_1$R$_2$=NMe$_2$)

This compound was prepared from compound cccc1 following the same procedure as described in Example 53 using the appropriate amine.
R$_f$=0.27 (98:2 dichloromethane/methanol).

Example 62

Synthesis of Compound ffff

To a cooled (ice-bath) solution of compound cccc (3.4 g, 16 mmol) in MeOH (36 mL) was added LiOH.H$_2$O (1.9 g, 45 mmol) in water (12 mL). The cooling bath was removed and the reaction mixture was stirred for an additional 1 h, diluted with water, acidified (1N HCl), and extracted several times into Et$_2$O. The combined organic layers were dried (MgSO$_4$) and concentrated in vacuo to generate a crude residue that on trituration with petroleum ether produced 2.3 g of compound ffff as a white solid. This material was directly used in the next step without further purification.
Analytical Data: $^1$H-NMR (DMSO-d$_6$) δ: 7.25-7.18 (m, 2H), 7.15-7.7.1 (m, 2H), 3.75 (m, 1H), 3.35 (s, 2H), 3.25 (dd, 2H), 2.85 (dd, 2H).

Example 63

Synthesis of Compound gggg

To a solution of compound ffff (2.3 g, 11 mmol) in acetic acid (30 mL) at room temperature was added aq. hydrogen peroxide (30%, 1.4 mL, 15 mmol). After stirring for 1 h, the reaction mixture was filtered and the residue was washed successively with acetic acid and ether. The solid was dried in vacuo to give 2.24 g of compound gggg that was directly used in the next step without further purification.
Analytical Data: $^1$H-NMR (DMSO-d$_6$) δ: 7.3-7.2 (m, 2H), 7.15 (broad, 2H), 3.95 (d, 1H), 3.85 (m, 1H), 3.6 (d, 1H), 3.4-3.15 (m, 3H), 3.0 (dd, 1H).

Example 64

Synthesis of Compound eeee1 (NR$_1$R$_2$=NH$_2$)

To a solution of compound dddd1 (NR$_1$R$_2$=NH$_2$) (0.64 g; 2.9 mmol) in acetic acid (7 mL) at room temperature was added aq. hydrogen peroxide (30% by wt, 0.38 mL, 3.7 mmol). The reaction mixture was stirred for additional 1 h, concentrated and purified by silica gel column chromatography (dichloromethane:methanol:: 9:1) to give 0.33 g of compound eeee1 (NR$_1$R$_2$=NH$_2$). R$_f$=0.43 (9:1 dichloromethane/methanol).
Analytical Data: $^1$H-NMR (DMSO-d$_6$) δ:7.5 (s, 1H), 7.25 (m, 2H), 7.2 (m, 2H), 7.0 (s, 1H), 3.7 (m, 1H), 3.3 (m, 1H), 3.2 (m, 2H), 3.0 (m, 2H), 2.75 (m, 1H), 2.5 (t, 2H).

Example 65

Synthesis of Compound eeee (NR$_1$R$_2$=N-pyrrolidinyl)

This compound was prepared from compound dddd (NR$_1$R$_2$=N-pyrrolidinyl) following the same procedure as described in Example 64. R$_f$=0.36 in 95:5 dichloromethane/methanol).
Analytical Data: $^1$H-NMR (DMSO-d$_6$) δ: 7.25 (m, 2H), 7.2 (broad, 2H), 3.85 (m, 3H), 3.5 (m, 2H), 3.45-3.15 (a series of m, 5H), 3.0 (m, 1H), 1.8 (broad m, 4H).

Example 66

Synthesis of Compound eeee (NR$_1$R$_2$=N-(4-hydroxy)piperidinyl)

To a cooled (ice-bath) solution of compound gggg (0.3 g; 1.3 mmol) in CH$_2$Cl$_2$ (25 mL) was successively added 4-piperidinol (0.15 g, 1.5 mmol), EDCI (0.28 g, 1.5 mmol) and HOBT (0.2 g; 1.5 mmol). The cooling bath was removed and the reaction mixture was stirred for 72 h. It was then successively washed with acid (1N HCl) and water, dried (MgSO$_4$) and concentrated in vacuo to generate a crude product that was purified by silica gel column chromatography (9:1 dichloromethane/methanol) to give 0.2 g of compound eeee. (NR$_1$R$_2$=N-(4-hydroxy)piperidinyl. R$_f$=0.43 (9:1 dichloromethane/methanol).
Analytical Data: $^1$H-NMR (CDCl$_3$) δ: 7.2 (broad, 4H), 4.05 (m, 1H), 3.95 (m, 2H), 3.80 (m, 2H), 3.55 (broad d, 1H), 3.3 (m, 4H), 3.15 (m, 1H), 1.95 (broad, 2H), 1.55 (broad, 2H).

Example 67

Synthesis of Compound eeee (NR$_1$R$_2$=NH$_2$)

This compound was prepared from compound dddd (NR$_1$R$_2$=NH$_2$) following the same procedure as described in Example 64. R$_f$=0.16 (95:5 dichloromethane/methanol).
Analytical Data: $^1$H-NMR (DMSO-d$_6$) δ: 7.70 (s, 1H), 7.30 (s, 1H), 7.25 (m, 1H), 7.20 (m, 1H), 7.10 (m, 2H), 3.80 (m, 1H), 3.60 (d, 1H), 3.50 (d, 1H), 3.4-3.1 (m, 3H), 3.0 (dd, 1H).

Example 68

Synthesis of Compound eeee (NR$_1$R$_2$=NMe$_2$)

This compound was prepared from compound dddd (NR$_1$R$_2$=NMe$_2$) following the same procedure as described in Example 64. R$_f$=0.28 (95:5 dichloromethane/methanol).
Analytical Data: $^1$H-NMR (DMSO-d$_6$) δ: 7.30 (m, 1H), 7.20 (m, 1H), 7.1 (broad, 2H), 3.95 (d, 2H), 3.85 (m, 1H), 3.45 (dd, 1H), 3.3-3.1 (m, 2H), 3.05 (s, 3H), 3.0 (m, 1H) 2.85 (s, 3H).

Example 69

Synthesis of Compound eeee (NR$_1$R$_2$=NHCHMe$_2$)

This compound was prepared from compound dddd (NR$_1$R$_2$=NHCHMe$_2$) following the same procedure as described in Example 64.
Analytical Data: $^1$H-NMR (DMSO-d$_6$) δ: 8.2 (broad d, 1H), 7.3-7.1 (m, 4H), 3.85 (m, 2H), 3.65 (d 1H), 3.5 (d, 1H), 3.4-3.2 (m, 4H), 3.0 (dd, 1H)1.1 (d, 6H).

Example 70

Synthesis of Compound eeee (NR$_1$R$_2$=N-(4-acetyl)-piperazinyl)

This compound was prepared from compound dddd (NR$_1$R$_2$=N-(4-acetyl)-piperazinyl) following the same procedure as described in Example 64.
Analytical Data: $^1$H-NMR (DMSO-d$_6$) δ: 7.3-7.1 (broad, 4H), 4.1-3.95 (broad, 2H), 3.85 (broad, 1H), 3.6-3.2 (broad m, 11H), 3.0 (dd, 1H), 2.0 (broad s, 3H).

Example 71

Synthesis of Compound eeee (NR$_1$R$_2$=NH(CH$_2$)$_2$—O—(CH$_2$)$_2$OH)

This compound was prepared from compound gggg following the same procedure as described in Example 66 using hydroxyethoxyethylamine in place of 4-piperidinol.
R$_f$=0.33 (9:1 dichloromethane/methanol).
Analytical Data: $^1$H-NMR (DMSO-d$_6$) δ: 8.3 (broad s, 1H), 7.3-7.1 (broad, 4H), 4.55 (broad s, 1H), 3.8 (broad, 1H), 3.75 (d, 1H), 3.6 (d, 1H), 3.55-3.1 (broad, 1H), 3.05 (broad dd, 1H).

Example 72

Synthesis of Compound eeee1 (NR$_1$R$_2$=N-pyrrolidinyl)

This compound was prepared from compound dddd1 (NR$_1$R$_2$=N-pyrrolidinyl) following the same procedure as described in Example 64. R$_f$=0.43 (93:7 dichloromethane/methanol).
Analytical Data: $^1$H-NMR (DMSO-d$_6$) δ: 7.3-7.1 (m, 4H), 3.75 (m, 1H), 3.45 (t, 2H), 3.4-3.2 (m, 5H), 3.1-2.9 (m, 2H), 2.8 (q, 1H), 2.7 (q, 2H), 1.9 (m, 2H), 1.7 (m, 2H).

Example 73

Synthesis of Compound eeee1 (NR$_1$R$_2$=NHCHMe$_2$)

This compound was prepared from compound dddd1 (NR$_1$R$_2$=NHCHMe$_2$) following the same procedure as described in Example 64. R$_f$=0.49 (9:1 dichloromethane/methanol).
Analytical Data: $^1$H-NMR (DMSO-d$_6$) δ: 7.9 (d, 1H), 7.3-7.2 (m, 2H), 7.1 (m, 2H), 3.8 (m, 1H), 3.75 (m, 1H), 3.4-3.1 (m, 3H), 3.05-2.9 (m, 2H), 2.75 (m, 1H), 2.5 (m, 2H), 1.05 (d, 6H).

Example 74

Synthesis of Compound eeee1 (NR$_1$R$_2$=NMe$_2$)

This compound was prepared from compound dddd1 (NR$_1$R$_2$=NMe$_2$) following the same procedure as described in Example 64. R$_f$=0.24 (95:5 dichloromethane/methanol).
Analytical Data: $^1$H-NMR (DMSO-d$_6$) δ: 7.3-7.2 (broad, 2H), 7.1 (broad, 2H), 3.75 (m, 1H), 3.4-3.2 (m, 2H), 3.05 (m, 2H), 3.0 (s, 3H), 2.8 (s, 3H), 2.75 (broad, 4H).

Example 75

Synthesis of Compound eeee (NR$_1$R$_2$=NE(CH$_2$)$_2$OH)

This compound was prepared from compound gggg following the same procedure as described in Example 66 using hydroxyethylamine in place of 4-piperidinol.
R$_f$=0.35 (9:1 dichloromethane/methanol).
Analytical Data: $^1$H-NMR (DMSO-d$_6$) δ: 8.3 (m, 1H), 7.3-7.2 (m, 2H), 7.1 (broad, 2H), 4.7 (t, 1H), 3.8 (m, 1H), 3.7 (d, 1H), 3.6 (d, 1H), 3.4 (m, 2H), 3.35-3.1 (m, 4H), 3.05 (dd, 1H).

Example 83

Synthesis of Compound eeee (NR$_1$R$_2$=NHCH$_2$CN)

This compound was prepared from compound cccc following the same procedure as described in Example 53 using the appropriate amine.
Analytical Data: $^1$H-NMR (DMSO-d$_6$) δ: 9.0 (t, 1H), 7.30-7.10 (broad m, 4H), 4.25 (d, 2H), 3.85 (m, 1H), 3.80 (d, 1H), 3.65 (d, 1H), 3.4-3.10 (m, 3H), 3.0 (dd, 1H).
MS: 285 (M+Na).

Scheme H: Tetrahydronaphthalenes

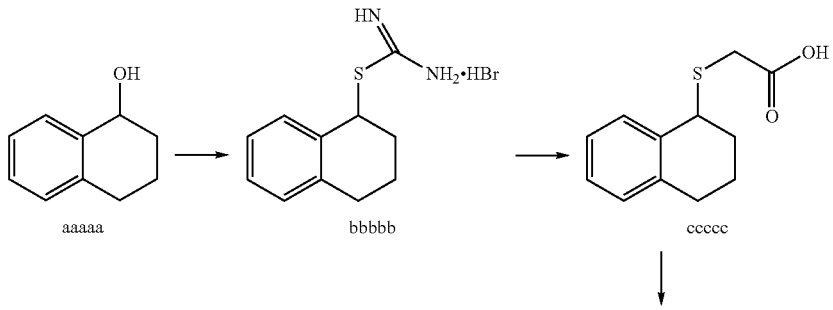

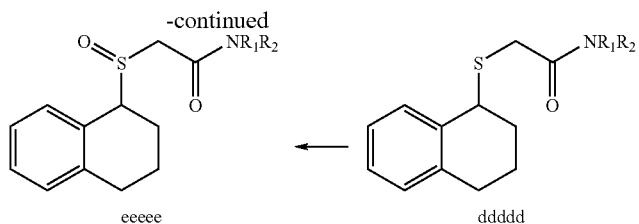

eeeee ← ddddd

Example 76

Synthesis of Compound ccccc

Starting with compound aaaaa, this compound was prepared following the same procedure as described in Example 1. Thus, the reaction between 10 g of compound aaaaa and 7.4 g of thiourea in the presence of 68 mL of 48% HBr generated 18.6 g of compound bbbbb (white solid; $R_t$: 7.16 min).

Subsequently, the reaction between 18.5 g of compound bbbbb and 6.6 g of chloroacetic acid in the presence of aq. NaOH produced 12.85 g of compound ccccc as an oil ($R_t$: 10.84 min).

Example 77

Synthesis of Compound ddddd ($NR_1R_2=NH_2$)

Starting with compound ccccc, this compound was prepared following the same procedure as described in Example 3. Thus, the reaction between 2 g of compound ccccc and 1.8 g of $NH_3$.HOBt-complex in the presence of EDCI generated 1.4 g of compound ddddd ($NR_1R_2=NH_2$, $R_1$: 9.43 min).

Example 78

Synthesis of Compound ddddd ($NR_1R_2=$N-pyrrolidinyl)

Starting with compound ccccc, this compound was prepared following the same procedure as described in Example 5. Thus, the reaction between 2 g of compound ccccc and 0.77 g of pyrrolidine in the presence of TBTU generated 2 g of compound ddddd ($NR_1R_2=$N-pyrrolidinyl, $R_t$: 12.04 min).

Example 79

Synthesis of Compound ddddd ($NR_1R_2=NMe_2$)

Starting with compound ccccc, this compound was prepared following the same procedure as described in Example 5. Thus, the reaction between 2 g of compound ccccc and 0.9 g of dimethylamine hydrochloride in the presence of TBTU generated 1.6 g of compound ddddd ($NR^1R_2=NMe_2$, $R_t$: 10.85 min).

Example 80

Synthesis of Compound eeeee ($NR_1R_2=NH_2$)

Starting with compound ddddd ($NR_1R_2=NH_2$), this compound was prepared following the same procedure as described in Example 10. Thus, the oxidation of 1.4 g of compound ddddd ($NR_1R_2=NH_2$) with aq. 50% $H_2O_2$ generated 1.18 g of compound eeeee ($NR_1R_2=NH_2$).

Analytical data: $^1$H-NMR (DMSO-$d_6$) δ 7.67 (d, 2H), 7.38-7.14 (m, 4H), 4.27 (t, 0.5H), 4.19 (t, 0.5H), 3.68-3.46 (m, 2H), 2.74 (t, 1H), 2.68 (t, 1H), 2.36-2.27 (m, 0.5H), 2.13-1.96 (m, 2H), 1.92-1.82 (m, 0.5H), 1.75-1.61 (m, 1H).

Example 81

Synthesis of Compound eeeee ($NR_1R_2=$N-pyrrolidinyl)

Starting with compound ddddd ($NR_1R_2=$N-pyrrolidinyl), this compound was prepared following the same procedure as described in Example 12. Thus, the oxidation of 2 g of compound ddddd ($NR_1R_2=$N-pyrrolidinyl) with aq. 50% $H_2O_2$ generated 0.37 g of compound eeeee ($NR_1R_2=$N-pyrrolidinyl).

Analytical data: $^1$H-NMR (DMSO-$d_6$) δ 7.44-7.42 (m, 1H), 7.24-7.12 (m, 3H), 4.34 (t, 0.25H), 4.28 (t, 0.75H), 3.92-3.80 (m, 2H), 3.55-3.28 (m, 4H), 2.75 (t, 0.5H), 2.69 (t, 1.5H), 2.38-2.31 (m, 1H), 2.08-1.97 (m, 2H), 1.90-1.75 (m, 4H), 1.73-1.63 (m, 1H).

Example 82

Synthesis of Compound eeeee ($NR_1R_2=NMe_2$)

Starting with compound ddddd ($NR_1R_2=NMe_2$), this compound was prepared following the same procedure as described in Example 14. Thus, the oxidation of 1.6 g of compound ddddd ($NR_1R_2=NMe_2$) with aq. 50% $H_2O_2$ generated 0.3 g of compound eeeee ($NR_1R_2=NMe_2$).

Analytical data: $^1$H-NMR (DMSO-$d_6$) δ 7.50-7.10 (m, 4H), 4.32 (t, 0.67H), 4.25 (t, 0.33H), 3.97 (s, 0.67H), 3.91 (s, 1.33H), 3.02 (s, 1H), 3.02 (s, 2H), 2.86 (s, 2H), 2.85 (s, 1H), 2.75 (t, 1.33H), 2.68 (t, 0.67H), 2.34-1.63 (m, 4H).

Illustrative of compounds encompassed by the present invention include those set forth in the following table. This list is meant to be representative only and is not intended to limit the scope of the invention in any way:

TABLE 1

| Example No. | Structure |
|---|---|
| 10 | ![structure] |

TABLE 1-continued

| Example No. | Structure |
|---|---|
| 11 | 2,3-dihydro-1H-indene with S(=O)-CH2-CH2-C(=O)-NH2 at position 1 |
| 12 | 2,3-dihydro-1H-indene with S(=O)-CH2-C(=O)-pyrrolidin-1-yl at position 1 |
| 13 | 2,3-dihydro-1H-indene with S(=O)-CH2-C(=O)-[pyrrolidine-2-carboxamide] at position 1 |
| 14 | 2,3-dihydro-1H-indene with S(=O)-CH2-C(=O)-N(CH3)2 at position 1 |
| 15 | 2,3-dihydro-1H-indene with S(=O)-CH2-C(=O)-[4-acetylpiperazin-1-yl] at position 1 |
| 16 | 2,3-dihydro-1H-indene with S(=O)-CH2-CH2-C(=O)-[4-acetylpiperazin-1-yl] at position 1 |
| 17 | 2,3-dihydro-1H-indene with S(=O)2-CH2-C(=O)-NH2 at position 1 |
| 19 | 2,3-dihydro-1H-indene with S(=O)-CH3 at position 1 |
| 26 | chroman-4-yl with S(=O)-CH2-C(=O)-NH2 |
| 27 | chroman-4-yl with S(=O)-CH2-C(=O)-pyrrolidin-1-yl |
| 28 | chroman-4-yl with S(=O)-CH2-C(=O)-N(CH3)2 |
| 29 | chroman-4-yl with S(=O)-CH2-C(=O)-NH-CH2-(pyridin-3-yl) |
| 30 | chroman-4-yl with S(=O)-CH2-C(=O)-NH-isobutyl |
| 33 | thiochroman-4-yl with S(=O)-CH2-C(=O)-N(CH3)2 |

TABLE 1-continued

| Example No. | Structure |
|---|---|
| 34 | (thiochromane-S-oxide with -S-CH2-C(O)-N(CH3)2) |
| 44 | (naphthalene-2-sulfinyl-CH2-C(O)-NH2) |
| 45 | (naphthalene-2-sulfinyl-CH2-C(O)-NH-CH(CH3)-C(O)-NH2) |
| 46 | (naphthalene-2-sulfinyl-CH2-C(O)-NH-CH2CH2-OH) |
| 47 | (naphthalene-2-sulfinyl-CH2-C(O)-pyrrolidine) |
| 48 | (naphthalene-2-sulfinyl-CH2-C(O)-NH-CH(C(O)NH2)-C(O)NH2) |
| 49 | (naphthalene-2-sulfinyl-CH2-C(O)-proline amide) |
| 64 | (indan-2-sulfinyl-CH2CH2-C(O)-NH2) |
| 65 | (indan-2-sulfinyl-CH2-C(O)-pyrrolidine) |
| 66 | (indan-2-sulfinyl-CH2-C(O)-4-hydroxypiperidine) |
| 67 | (indan-2-sulfinyl-CH2-C(O)-NH2) |
| 68 | (indan-2-sulfinyl-CH2-C(O)-N(CH3)2) |
| 69 | (indan-2-sulfinyl-CH2-C(O)-NH-iPr) |
| 70 | (indan-2-sulfinyl-CH2-C(O)-N-acetylpiperazine) |
| 71 | (indan-2-sulfinyl-CH2-C(O)-NH-CH2CH2-O-CH2CH2-OH) |

TABLE 1-continued

| Example No. | Structure |
|---|---|
| 72 | (indane)-S(=O)-CH2CH2-C(=O)-N(pyrrolidine) |
| 73 | (indane)-S(=O)-CH2CH2-C(=O)-NH-iPr |
| 74 | (indane)-S(=O)-CH2CH2-C(=O)-N(CH3)2 |
| 75 | (indane)-S(=O)-CH2-C(=O)-NH-CH2CH2-OH |
| 80 | (tetralin)-S(=O)-CH2-C(=O)-NH2 |
| 81 | (tetralin)-S(=O)-CH2-C(=O)-N(pyrrolidine) |
| 82 | (tetralin)-S(=O)-CH2-C(=O)-N(CH3)2 |
| 83 | (indane)-S(=O)-CH2-C(=O)-NH-CH2-CN |

Utility

The present invention provides a method of treating diseases and conditions in a subject in need thereof comprising administering to said subject a therapeutically effective amount of a compound of the present invention. For example, the compounds of the present invention may be useful for the treatment of diseases, such as excessive sleepiness, promotion and/or improvement of wakefulness (preferably improvement of wakefulness in patients with excessive sleepiness associated with narcolepsy, sleep apnea (preferably obstructive sleep apnea/hypopnea) and shift work disorder), treatment of Parkinson's disease, Alzheimer's disease, cerebral ischemia, stroke, eating disorders, attention deficit disorder ("ADD"), attention deficit hyperactivity disorder ("ADHD"), depression, schizophrenia, fatigue (preferably fatigue associated with cancer or neurological diseases, such as multiple sclerosis and chronic fatigue syndrome), stimulation of appetite and weight gain and improvement of cognitive dysfunction.

Methodology: Evaluation of Wake Promoting Activity in Rats

The methodology utilized for evaluating wake promoting activity of test compounds is based on that described by Edgar and Seidel, *Journal of Pharmacology and Experimental Therapeutics*, 283:757-769, 1997, and incorporated herein in its entirety by reference.

Animal Surgery. Adult, male Wistar rats (275-320 g from Charles River Laboratories, Wilmington, Mass.) were anesthetized (Nembutal, 45 mg/kg, ip.) and surgically prepared with implants for recording of chronic EEG (encephalographic) and EMG (electromyographic) recording. The EEG implants were made from commercially available components (Plastics One, Roanoke, Va.). EEG signals were recorded from stainless steel screw electrodes: 2 frontal (+3.0 mm AP from bregma, ±2.0 mm ML), and 2 occipital (−4.0 mm AP from bregma, ±2.0 mm ML). Two Teflon-coated stainless steel wires were positioned under the nuchal trapezoid muscles for EMG recording. All electrode leads were inserted into a connector pedestal and the pedestal affixed to the skull by application dental acrylic. Antibiotic was administered post surgically and antibiotic cream was applied to the wound edges to prevent infection. At least one week elapsed between surgery and recording.

Recording environment. Postsurgically, rats were housed in pairs in an isolated room. Food and water were available ad libitum, ambient temperature was 21° C., and humidity was 55%. At least 24 hrs prior to recording, they were placed in Nalgene containers (31×31×31 cm) with a wire-grid top, and entry to the room was prohibited during the day of recording except for dosing. The containers were placed on a rack with two shelves, 4 containers per shelf. Fluorescent overhead room lights were set to a 24 hr. light/dark cycle (on at 7 AM, off at 7 PM). Light levels inside the containers were 38 and 25 lux for the top and bottom shelves respectively. Background white-noise (68 db inside the containers) was present in the room to mask ambient sounds.

Data acquisition. EEG and EMG signals were led via cables to a commutator (Plastics One) and then to pre-amplifiers (model 1700, A-M Systems, Carlsborg, Wash.). EEG and EMG signals were amplified (10K and 1K respectively) and band pass filtered between 0.3 and 500 Hz for EEG and between 10 and 500 Hz for EMG. These signals were digitized at 128 samples per second using ICELUS sleep research software (M. Opp, U. Texas; see Opp, Physiology and Behavior 63:67-74, 1998, and Imeri, Mancia, and Opp, *Neuroscience* 92:745-749, 1999, incorporated by reference herein in their entirety) running under Labview 5.1 software and data acquisition hardware (PCI-MIO-16E-4; National Instruments, Austin, Tex.). On the day of dosing, data was recorded for 6 to 10 hours beginning at 11 AM.

Drug administration and study design. Compounds were evaluated on groups of from 4 to 8 rats carried out over one or two separate test sessions. Each animal was tested with a different compound or vehicle for up to 10 weeks with at least 7 days between successive tests. A vehicle group was included in all experiments, and each animal received vehicle every $4^{th}$ test. Test compounds were suspended in sterile 0.25% methylcellulose (pH=6.2; Upjohn Co., Kalamazoo, Mich.) at 30 mg/mL. Unless otherwise noted, compounds were administered at a single dose of 100 mg/kg. Dosing was carried out at noon, while the rats were predominantly asleep. Each rat was lifted out of its container, given an intraperitoneal injection in a volume of 5 mL/kg, and replaced. Dosing required approximately 30 sec per rat.

Sleep/wake scoring. Sleep and wake activity were determined using a procedure involving manual scoring using the ICELUS software, followed by application of an autoscoring program written in Microsoft Excel (Microsoft, Inc., Redmond, Wash.) The ICELUS program displays the EEG and EMG data in blocks of 6 sec along with the EEG frequency spectrum (FFT) amplitudes. Arousal state was scored as awake, rapid eye-movement (REM), or slow-wave or non-REM sleep according to visual analysis of EEG frequency and amplitude characteristics and EMG activity (Opp and Krueger, 1994; Van Gelder, et al., 1991; Edgar, et al., 1991, 1997; Seidel, et al, 1995, incorporated by reference herein in their entirety). Essentially, waking activity consists of relatively low-amplitude EEG activity with relatively lower power in the frequency band from 0.5-6 Hz, accompanied by moderate to high level EMG activity. In a particular waking state ("theta-waking"), EEG power can be relatively focused in the 6-9 Hz (theta) range, but significant EMG activity is always present. NREM sleep is characterized by relative high-amplitude EEG activity with relatively greater power in the low frequency band from 0.5-6 Hz, accompanied by little or no EMG activity. REM sleep is characterized by moderate and constant amplitude EEG focused in the theta (6-9 Hz) range, similar to waking theta, but with no EMG activity.

To convert the raw data to sleep/wake stage scores, normally the first hour of activity (prior to dosing) is manually scored into sleep, wake, or REM states. Subsequent activity is evaluated using a computer algorithm which takes into account FFT amplitudes, theta-band activity, and EMG activity for each 6 second epoch. An iterative procedure is used to adjust 3 different parameter thresholds until the first hour of data scored by the computer algorithm matches as closely as possible with the manual values. These parameter values are then used to score the remaining activity. The data are then reduced to "wake" (wake+waking theta activity) or "sleep" (REM+non-REM) for each 6 sec epoch. The time spent awake was then calculated for each 5 and 30 min interval relative to the specific time of dosing (approximately 12:00 noon).

Data Analysis and Statistics.

Two basic outcome measures were used to ascertain whether a compound exhibited wake-enhancing activity. The first was the percent time spent awake (0-100%) for each 30 min period following dosing. The second was the sum in minutes of the time spent awake for the first 6 half-hour periods following dosing (3 hr AUC; maximum 180 min).

For purposes of ascertaining activity of a test compound, wake activity values were compared against corresponding vehicle values. The vehicle values were of two types. The first type was the corresponding within-experiment vehicle, that is, a value derived from the vehicle group run concurrently with the test compound. A second reference vehicle value was also used for comparison, which consisted of the mean 3 hr AUC value calculated from 234 animals in 59 separate experiments carried out during the same time period as the evaluations of the test compounds (mean±SD=69.22±20.12; 95% confidence limits=66.63-71.81). Two-tailed, unpaired t-tests were performed on the wake time values for drug versus vehicle treated animals, and compounds with $p \leq 0.05$ were deemed significantly wake-promoting. A test compound was considered active as a wake promoting agent if it met one or more of the following three criteria.

(i) The 3 hr AUC value for the test compound was significantly greater ($p \leq 0.05$) than the mean wake value for the reference vehicle group (N=234).

(ii) The 3 hr AUC value for the test compound was significantly greater ($p \leq 0.05$) than the corresponding value for the within-experiment vehicle group.

(iii) One or more of the half-hour wake time values from 0.5 to 2 hrs after dosing were significantly greater ($p \leq 0.05$) in the test compound group compared to the within-experiment vehicle group.

Results.

Compounds of the invention either have demonstrated or are expected to demonstrate utility for wake promoting activity.

REFERENCES

The following references, to the extent that they provide exemplary procedural or other details supplementary to those set forth herein, are specifically incorporated in their entirety herein by reference:

Touret, et al., *Neuroscience Letters*, 189:43-46, 1995.
Van Gelder, R. N. et al., *Sleep* 14:48-55, 1991.
Edgar, D. M., *J. Pharmacol. Exp. Ther.* 282:420-429, 1997.
Edgar and Seidel, *J. Pharmacol. Exp. Ther.*, 283:757-69, 1997.
Hemant et al., *Psychopharmacology*, 103:28-32, 1991.
Lin et al., *Brain Research*, 591:319-326, 1992.
Opp and Krueger, *American Journal of Physiology* 266: R688-95, 1994
Panckeri et al., *Sleep*, 19(8):626-631, 1996.
Seidel, W. F., et al., *J. Pharmacol. Exp. Ther.* 275:263-273, 1995.
Shelton et al., *Sleep* 18(10):817-826, 1995.
Welsh, D. K., et al., *Physiol. Behav.* 35:533-538, 1985.

Dosage and Formulation.

The compounds of the present invention can be administered for therapeutic purposes by any means that results in the contact of the active agent with the agent's site of action in a subject. The compounds may be administered by any conventional means available for use in conjunction with pharmaceuticals, either as individual therapeutic agents or in a combination with other therapeutic agents, such as, for example, analgesics, or in combination with antidepressants, including but are not limited to tricyclic antidepressants ("TCAs"), Selective Serotonin Reuptake Inhibitors ("SSRIs"), Serotonin and Noradrenalin Reuptake Inhibitors ("SNRIs"), Dopamine Reuptake Inhibitors ("DRIs"), Noradrenalin Reuptake Inhibitors ("NRUs"), Dopamine, Serotonin and Noradrenalin Reuptake Inhibitors ("DSNRIs") and Monoamine Oxidase Inhibitors ("MAOIs") including reversible inhibitors of monoamine oxidase type A (RIMAs). The compounds of the present invention are preferably administered in therapeutically effective amounts for the treatment of the diseases and disorders described herein.

A therapeutically effective amount can be readily determined by the attending diagnostician, as one skilled in the art, by the use of conventional techniques. The effective dose will vary depending upon a number of factors, including the pharmacodynamics of the active agent, the type and extent of progression of the disease or disorder, the age, weight and health of the particular patient, the formulation of the active and its mode and frequency of administration, and the desired effect with a minimization of side effects. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A typical daily dose for adult humans can range from about 1 to about 1000 mg of the active agent, particularly from about 1 to about 400 mg, and including 25, 50, 85, 100, 150, 170, 200, 255, 250, 255, 340, 400, 425, 500, 600, 700, 750, 800, and 900 mg doses, and equivalent doses for a human child.

The compounds may be administered in one or more unit dose forms, and they may be administered in a single daily dose or in two, three or four doses per day. The unit dose ranges from about 1 to about 1000 mg, particularly from about 1 to about 400 mg, and including 25, 50, 85, 100, 150, 170, 200, 255, 250, 255, 340, 400, 425, 500, 600, 700, 750, 800, and 900 mg unit doses, and equivalent unit doses for a human child. In particular, the unit dosages range from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The active agent may be present in about 0.5-95% by weight of the composition. The excipients are selected on the basis of the chosen route of administration and standard pharmaceutical practice, as described, for example, in *Remington: The Science and Practice of Pharmacy*, 20$^{th}$ ed.; Gennaro, A. R., Ed.; Lippincott Williams & Wilkins: Philadelphia, Pa., 2000.

The compositions can be prepared for administration by oral means, including tablets, pills, powders, capsules, troches and the like; parenteral means, including intravenous, intramuscular, and subcutaneous means; topical or transdermal means, including patches, creams, ointments, lotions, pastes, gels, solutions, suspensions, aerosols, and powders and the like; transmucosal means, including nasal, rectal, vaginal, sublingual and buccal means; ophthalmic or inhalation means. Preferably the compositions are prepared for oral administration, particularly in the form of tablets, capsules or syrups; parenteral administration, particularly in the form of liquid solutions, suspensions or emulsions; intranasal administration, particularly in the form of powders, nasal drops, or aerosols; or for topical use, such as patches, creams, ointments, and lotions.

For oral administration, the tablets, pills, powders, capsules, troches and the like can contain one or more of the following: diluents or fillers such as starch, or cellulose; binders such as microcrystalline cellulose, gelatins, or polyvinylpyrrolidone; disintegrants such as starch or cellulose derivatives; lubricants such as talc or magnesium stearate; glidants such as colloidal silicon dioxide; sweetening agents such as sucrose or saccharin; and flavoring agents such as peppermint or cherry flavoring. Capsules may contain any of the above ingredients, and may also contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be provided as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers; suspending agents; thickening agents; and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be provided as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably provided as unit-dose suppositories, with a solid based carrier, such as cocoa butter, and may include a salicylate.

The compositions of the present invention may be formulated to control and/or delay the release of the active agent(s). Such controlled-, delayed, sustained-, or extended-release compositions are well-known in the art, and may include, for example, reservoir or matrix diffusion products, as well as dissolution systems. Some compositions may utilize, for example biocompatible, biodegradable lactide polymer, lactide/glycolide copolymer, or polyoxyethylene-polyoxypropylene copolymers as excipients.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A method of treating excessive sleepiness in a subject in need thereof comprising administering to said subject a therapeutically effective amount of a compound of formula (IV):

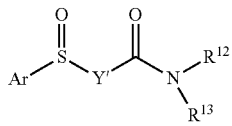

wherein
Ar is

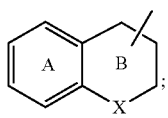

wherein X is a bond, $CH_2$, or O;
ring A optionally substituted with one to three groups selected from F, Cl, Br, I, $OR^{21}$, $OR^{25}$, $NR^{23}R^{24}$, NHOH, $NO_2$, CN, $C_1$-$C_6$ alkyl, and $C(=O)R^{22}$;
Y' is $C_1$-$C_4$ alkylene, wherein said alkylene group is optionally substituted with an $R^{20}$ group;
$R^{12}$ and $R^{13}$ at each occurrence are each independently selected from H, and $C_1$-$C_6$ alkyl, wherein said alkyl group can optionally be substituted with one or two CN, $OR^{21}$, $O(CH_2)_{1-4}OR^{21}$, $C(=O)N(R^{21})_2$, or pyridyl groups, or $R^{12}$ and $R^{13}$, together with the nitrogen to which they are attached, form a pyrrolidinyl, piperidinyl, or piperazinyl ring, optionally substituted with $OR^{21}$, $C(=O)N(R^{21})_2$, or $C(=O)R^{21}$;
$R^{20}$ at each occurrence is independently selected from F, Cl, Br, I, $OR^{21}$, $OR^{25}$, $NR^{23}R^{24}$, NHOH, $NO_2$, CN, and $CF_3$;
$R^{21}$ at each occurrence is independently selected from H and $C_1$-$C_6$ alkyl;
$R^{22}$ at each occurrence is independently selected from $C_1$-$C_6$ alkyl, and phenyl;
$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;
$R^{25}$ at each occurrence is independently the residue of an amino acid after the hydroxyl group of the carboxyl group is removed;
or a stereoisomeric form, mixture of stereoisomeric forms or pharmaceutically acceptable salt thereof.

2. The method of claim 1, wherein X is a bond, Y' is $CH_2$, or $CH_2CH_2$, and $R^{12}$ and $R^{13}$ is H, $C_1$-$C_4$ alkyl, optionally substituted with a CN, $OR^{21}$, $O(CH_2)_{1-4}OR^{21}$ group; or $R^{12}$ and $R^{13}$, together with the nitrogen to which they are attached, form a pyrrolidinyl, piperidinyl, or piperazinyl ring, optionally substituted with $OR^{21}$, $C(=O)N(R^{21})_2$, or $C(=O)R^{21}$ group.

3. The method of claim 1, wherein X is $CH_2$, Y' is $CH_2$, and $R^{12}$ and $R^{13}$ is H or $C_1$-$C_4$ alkyl, or $R^{12}$ and $R^{13}$, together with the nitrogen to which they are attached, form a pyrrolidinyl ring.

4. The method of claim 1, wherein X is O, Y' is $CH_2$, and $R^{12}$ and $R^{13}$ is H or $C_1$-$C_4$ alkyl, optionally substituted with a pyridyl group; or $R^{12}$ and $R^{13}$, together with the nitrogen to which they are attached, form a pyrrolidinyl ring.

5. The method of claim 1 wherein the compound is selected from the following table:

| Example | Structure |
| --- | --- |
| 10 | 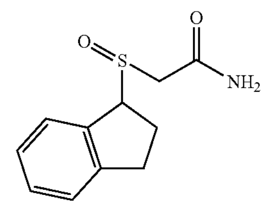 |
| 11 | 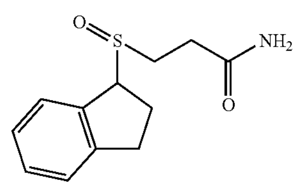 |
| 12 | 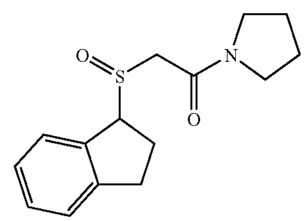 |
| 14 | 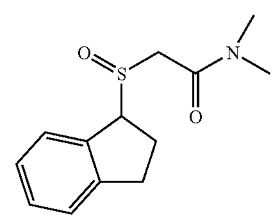 |
| 15 | 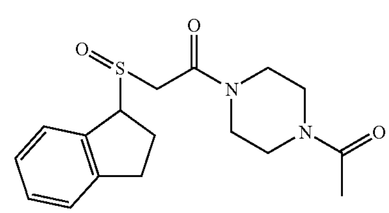 |
| 16 | 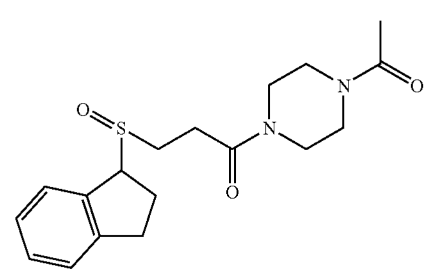 |

| Example | Structure |
|---|---|
| 19 | (1-(methylsulfinyl)-2,3-dihydro-1H-indene) |
| 26 | (chroman-4-yl sulfinyl acetamide) |
| 28 | (2-(chroman-4-ylsulfinyl)-N,N-dimethylacetamide) |
| 29 | (2-(chroman-4-ylsulfinyl)-N-(pyridin-3-ylmethyl)acetamide) |
| 30 | (2-(chroman-4-ylsulfinyl)-N-isobutylacetamide) |
| 64 | (3-(2,3-dihydro-1H-inden-2-ylsulfinyl)propanamide) |
| 66 | (1-(4-hydroxypiperidin-1-yl)-2-(2,3-dihydro-1H-inden-2-ylsulfinyl)ethanone) |

| Example | Structure |
|---|---|
| 69 | (2-(2,3-dihydro-1H-inden-2-ylsulfinyl)-N-isopropylacetamide) |
| 71 | (2-(2,3-dihydro-1H-inden-2-ylsulfinyl)-N-(2-(2-hydroxyethoxy)ethyl)acetamide) |
| 72 | (3-(2,3-dihydro-1H-inden-2-ylsulfinyl)-1-(pyrrolidin-1-yl)propan-1-one) |
| 73 | (3-(2,3-dihydro-1H-inden-2-ylsulfinyl)-N-isopropylpropanamide) |
| 75 | (2-(2,3-dihydro-1H-inden-2-ylsulfinyl)-N-(2-hydroxyethyl)acetamide) |
| 80 | (2-(1,2,3,4-tetrahydronaphthalen-1-ylsulfinyl)acetamide) |
| 82 | (2-(1,2,3,4-tetrahydronaphthalen-1-ylsulfinyl)-N,N-dimethylacetamide) or |

-continued
| Example | Structure |
|---------|-----------|
| 83 | 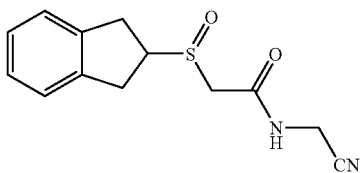 |
or a stereoisomeric form, mixture of stereoisomeric forms or pharmaceutically acceptable salt thereof.
6. The method of claim 5, wherein the excessive sleepiness is associated with narcolepsy, obstructive sleep apnea or shift work disorder.
* * * * *